US011738213B2

(12) United States Patent
Timmer et al.

(10) Patent No.: US 11,738,213 B2
(45) Date of Patent: *Aug. 29, 2023

(54) PARTICLE THERAPY SYSTEMS, DEVICES, AND METHODS FOR BEAM TRANSPORTATION

(71) Applicants: VARIAN MEDICAL SYSTEMS, INC., Palo Alto, CA (US); Varian Medical Systems Particle Therapy GMBH & CO.KG, Troisdorf (DE)

(72) Inventors: Jan H. Timmer, San Jose, CA (US); Juergen Schultheiss, Cologne (DE)

(73) Assignees: VARIAN MEDICAL SYSTEMS, INC., Palo Alto, CA (US); VARIAN MEDICAL SYSTEMS PARTICLE THERAPY GMBH & CO. KG, Troisdorf (DE)

( * ) Notice: Subject to any disclaimer, the term of this patent is extended or adjusted under 35 U.S.C. 154(b) by 927 days.

This patent is subject to a terminal disclaimer.

(21) Appl. No.: 16/704,525

(22) Filed: Dec. 5, 2019

(65) Prior Publication Data

US 2020/0108279 A1 Apr. 9, 2020

Related U.S. Application Data

(63) Continuation of application No. 15/503,451, filed as application No. PCT/US2015/046239 on Aug. 21, 2015, now Pat. No. 10,532,229.

(Continued)

(51) Int. Cl.

| | |
|---|---|
| ***A61N 5/01*** | (2006.01) |
| ***H05H 7/04*** | (2006.01) |
| ***A61N 5/10*** | (2006.01) |

(52) U.S. Cl.

CPC ............. *A61N 5/1081* (2013.01); *A61N 5/01* (2013.01); *H05H 7/04* (2013.01);

(Continued)

(58) Field of Classification Search

CPC .......... A61N 5/10–1084; A61N 5/1077–1087; H05H 2007/007; H05H 2007/045;

(Continued)

(56) References Cited

U.S. PATENT DOCUMENTS

| | | | |
|---|---|---|---|
| 4,870,287 | A | 9/1989 | Cole et al. |
| 5,523,659 | A | 6/1996 | Swenson |

(Continued)

FOREIGN PATENT DOCUMENTS

| | | | |
|---|---|---|---|
| CN | 102387836 | A | 3/2012 |
| CN | 103153397 | A | 6/2013 |

(Continued)

OTHER PUBLICATIONS

International Search Report and Written Opinion dated Jan. 8, 2016, in International Application No. PCT/US2015/046239.

(Continued)

*Primary Examiner* — Thaddeus B Cox
*Assistant Examiner* — Marc D. Honrath
(74) *Attorney, Agent, or Firm* — Potomac Law Group, PLLC

(57) ABSTRACT

A beam transport assembly conveys a particle beam from a particle source to an irradiation nozzle, which rotates about a swivel axis at the horizontal input of the nozzle. A support can move horizontally in a plane perpendicular to the swivel axis. The beam transport assembly can change a path length of the particle beam so as to follow a vertical location of the swivel axis of the irradiation nozzle with respect to the support. A controller can coordinate the path length change of the particle beam, rotation of the irradiation nozzle about (Continued)

the swivel axis, and/or horizontal motion of the support to provide irradiation of a supported object from various angles in the plane perpendicular to the swivel axis while maintaining the irradiation nozzle at a constant distance from the supported object.

12 Claims, 13 Drawing Sheets

Related U.S. Application Data

(60) Provisional application No. 62/040,657, filed on Aug. 22, 2014.

(52) U.S. Cl.
CPC ................ *A61N 2005/1087* (2013.01); *H05H 2007/043* (2013.01); *H05H 2007/046* (2013.01)

(58) Field of Classification Search
CPC .... H05H 2007/046; H05H 7/00–15/00; H05H 2277/10–116; H05H 7/001; H05H 2007/002–008; H05H 7/04; H05H 2007/041–048; H05H 7/12; H05H 2007/122–127; H05H 7/14–20; G21K 5/00–10
See application file for complete search history.

(56) References Cited

U.S. PATENT DOCUMENTS

| | | | | |
|---|---|---|---|---|
| 6,172,463 | B1 | 1/2001 | Cutler et al. | |
| 6,683,318 | B1 | 1/2004 | Haberer et al. | |
| 7,432,516 | B2 | 10/2008 | Peggs et al. | |
| 8,053,746 | B2 | 11/2011 | Timmer et al. | |
| 9,168,392 | B1 | 10/2015 | Balakin | |
| 2004/0184579 | A1 | 9/2004 | Mihara et al. | |
| 2006/0193435 | A1 | 8/2006 | Hara et al. | |
| 2007/0170994 | A1 | 7/2007 | Peggs et al. | |
| 2010/0027745 | A1 | 2/2010 | Balakin | |
| 2010/0038552 | A1* | 2/2010 | Trbojevic | H05H 7/04 250/396 ML |
| 2010/0133446 | A1 | 6/2010 | Balakin | |
| 2011/0017920 | A1 | 1/2011 | Goer et al. | |
| 2011/0182410 | A1 | 7/2011 | Balakin | |
| 2011/0196226 | A1* | 8/2011 | Gross | A61N 5/1049 600/411 |
| 2012/0119105 | A1 | 5/2012 | Iwata | |
| 2012/0203490 | A1 | 8/2012 | Sayeh et al. | |
| 2012/0313003 | A1 | 12/2012 | Trbojevic | |
| 2013/0015364 | A1 | 1/2013 | Mackinnon et al. | |
| 2013/0178690 | A1 | 7/2013 | Masumoto et al. | |
| 2013/0289330 | A1 | 10/2013 | Haruna et al. | |
| 2014/0048718 | A1 | 2/2014 | Sano | |
| 2014/0094643 | A1* | 4/2014 | Gall | A61N 1/44 600/1 |

FOREIGN PATENT DOCUMENTS

| | | | | |
|---|---|---|---|---|
| CN | 103492025 | A | 1/2014 | |
| DE | 202006019307 | U1 | 5/2008 | |
| EP | 0 986 070 | A1 | 3/2000 | |
| JP | 2001-178834 | A | 7/2001 | |
| JP | 2013-240575 | A | 12/2013 | |
| WO | WO 9606445 | A1 | 2/1996 | |
| WO | WO 0028797 | A1 | 5/2000 | |
| WO | WO 2015/090555 | A1 | 6/2015 | |
| WO | WO-2015090555 | A1 * | 6/2015 | A61N 5/107 |

OTHER PUBLICATIONS

International Search Report and Written Opinion dated Feb. 19, 2015, in International Application No. PCT/EP2014/003360.

European Search Report dated Mar. 12, 2018, in European Application No. 15833367.4.

Office Action and Search Report dated Jun. 4, 2018, in Chinese Patent Application No. 2015800450152.

Office Action and Search Report dated Apr. 28, 2018, in Chinese Patent Application No. 2014800491020.

Office Action dated Aug. 6, 2018, in Japanese Patent Application No. 2016-559512.

Office Action dated Aug. 2, 2019, in Chinese Patent Application No. 2015800450152.

Office Action dated Jan. 22, 2019, in European Application No. 15833367.4.

Office Action and Search Report dated Mar. 5, 2019, in Chinese Patent Application No. 2015800450152.

Office Action and Search Report dated Dec. 3, 2018, in Chinese Patent Application No. 2014800491020.

Office Action dated Mar. 31, 2021, in Chinese Patent Application No. 202010188052.1.

Office Action dated Oct. 19, 2021, in Chinese Patent Application No. 202010188052.1.

Office Action dated Jan. 18, 2021, in European Patent Application No. 15833367.4.

* cited by examiner

PARTICLE THERAPY SYSTEMS, DEVICES, AND METHODS FOR BEAM TRANSPORTATION

CROSS-REFERENCE TO RELATED APPLICATIONS

This application claims the benefit of U.S. Provisional Application No. 62/040,657, filed Aug. 22, 2014, which is hereby incorporated by reference herein its entirety.

FIELD

The present disclosure relates generally to delivering a particle beam for irradiation of an object, such as providing particle therapy to a patient, and, more particularly, to systems, methods, and devices for transporting a particle beam for subsequent irradiation.

BACKGROUND

A beam of high-energy particles can be used to deliver a therapy to a patient, for example, as medical treatment for a patient's cancer. Particles in the beam (e.g., protons) can have energies greater than 20 MeV, for example, between 70 MeV and 250 MeV. The particles can be generated in a particle accelerator and delivered to a patient at a treatment station where the particle beam emanates from an irradiation nozzle. The nozzle directs the beam at the patient on a support, for example, an adjustable gurney or chair that holds the patient in position relative to the particle beam. The depth of particle penetration and the position of the particle beam may be varied in order to treat a three-dimensional volume within a patient. Depth control can be achieved by varying the energy of the particles. A gantry is used to rotate the irradiation nozzle about the patient to irradiate the desired volume within the patient from different angles.

A configuration of a particle therapy system 100 is shown in FIG. 1A. The particle therapy system 100 receives a particle beam 114, for example, a proton beam, from a particle beam source (not shown), such as a particle accelerator. The particle beam 114 is transported from the particle beam source via a beam transport system (not shown) that provides the beam 114 to the gantry 108 for irradiating a patient 102. The beam transport system can include a vacuum tube and beam control components, such as, quadrupole magnets that focus the particle beam and dipole magnets that deflect the particle beam.

The particle beam 114 enters the gantry 108 via a rotating vacuum seal 112. Within the gantry 108, the particle beam can follow a serpentine path to an irradiation nozzle 122, which redirects the particle beam along path 110 for irradiation of the patient 102. Magnets 118 and 120 within gantry 108 redirect the particle beam from the vacuum seal 112 to the irradiation nozzle 122. The magnets 118 and 120 rotate with the irradiation nozzle 122, while the relative positions (i.e., the vertical distance perpendicular to axis 116 and the horizontal distance parallel to axis 116 between the magnets 118 and 120) between magnets 118 and 120 remain otherwise fixed even though their orientation changes.

A patient support 104 positions the patient 102 aligned with a rotation axis 116 of the gantry 108. The irradiation nozzle 122 is rotated around the rotation axis 116 by the gantry 108 to irradiate the treatment volume within the patient from different angles. The gantry 108 can be rotated such that the beam 110 hits the treatment isocenter of the patient 102 without the need to change magnetic field strengths of the magnets. For example, as illustrated in FIG. 1B, the gantry can move the irradiation nozzle 122 from a vertical position 130 above the patient (e.g., 0° rotation), to a horizontal position 132 (e.g., 90° rotation), to a vertical position 134 below the patient (e.g., 180° rotation), to another horizontal position 136 on an opposite side of the patient (e.g., 225° rotation), and to various points in between. To accommodate the rotation of the irradiation nozzle at a constant radius with respect to the patient 102, the patient support 104 holds the patient 102 at an elevated position above the floor 106. Alternatively or additionally, the gantry 108 may have a portion that lies below the floor 106 to minimize or at least reduce the height at which the patient 102 is positioned.

As a result of the above described operation, particle therapy gantries can be heavy and have a footprint significantly larger than conventional photon therapy gantries. Such known gantry designs require complex and bulky structures, in particular in order to allow the gantry to be rotated through a full 360° around the irradiation object.

SUMMARY

Particle beam systems, devices, and methods for beam transportation are disclosed herein. In one or more exemplary embodiments of the disclosed subject matter, a beam transport assembly for conveying a particle beam comprises a first beam tube, a second beam tube, one or more first focusing magnets, one or more second focusing magnets, and an expandable portion. The first beam tube can have a first interior volume maintained under vacuum. The second beam tube can have a second interior volume maintained under vacuum. The second beam tube can be axially spaced from the first beam tube. The one or more first focusing magnets can be arranged along the first beam tube. The one or more second focusing magnets can be arranged along the second beam tube. The expandable portion can couple the first beam tube to the second beam tube such that the particle beam can be conveyed therebetween. The expandable portion can be configured to accommodate changed positions of the first and second beam tubes with respect to each other so as to alter a path length for the particle beam through the beam transport assembly.

In one or more exemplary embodiments of the disclosed subject matter, a system for irradiating an object with a particle beam includes a beam transport assembly, an irradiation nozzle, a support, and a controller. The beam transport assembly can convey the particle beam from a particle source along a substantially vertical direction and can redirect the particle beam to a horizontal input. The irradiation nozzle can be coupled to the beam transport assembly to receive the particle beam at the horizontal input. The irradiation nozzle can be configured to redirect the particle beam toward the object and to rotate about a swivel axis at the horizontal input. The support can be constructed to support the object with respect to the irradiation nozzle and to move horizontally in a plane perpendicular to the swivel axis. The controller can be configured to coordinate movements of the beam transport assembly, the irradiation nozzle, and the support. The beam transport assembly can be constructed to change a path length of the particle beam so as to follow a vertical location of the swivel axis of the irradiation nozzle with respect to the support. The controller can be configured to coordinate the path length change of the particle beam, rotation of the irradiation nozzle about the swivel axis, and/or horizontal motion of the support to provide irradiation of the supported object from various angles in the plane perpendicular to the swivel axis while maintaining the irradiation nozzle at a constant distance from the supported object.

In one or more exemplary embodiments of the disclosed subject matter, a method for irradiating an object can include conveying a particle beam from a particle source along a beam transport assembly to a horizontal input of an irradiation nozzle. The irradiation nozzle can be configured to rotate about a swivel axis at the horizontal input. The method can further include redirecting the particle beam from the horizontal input within the irradiation nozzle and directing the particle beam from the irradiation nozzle to irradiate the object arranged on a support from a first position. The method can also include changing a path length of the particle beam in the beam transport assembly so as to follow a vertical location of the swivel axis of the irradiation nozzle with respect to the support.

In one or more exemplary embodiments of the disclosed subject matter, a non-transitory computer-readable storage medium and a computer processing system can be provided. A sequence of programmed instructions for controlling a system to irradiate an object with a particle beam can be embodied on the computer-readable storage medium. The computer processing system can execute the sequence of programmed instructions embodied on the computer-readable storage medium to cause the computer processing system to control one or more focusing magnets of a beam transport assembly to convey a particle beam from a particle source along the beam transport assembly to a horizontal input of an irradiation nozzle; to control one or more deflecting magnets to redirect the particle beam from the horizontal input within the irradiation nozzle and to direct the particle beam from the irradiation nozzle to irradiate the object arranged on a support from a first position; and to control the beam transport assembly to change a path length of the particle beam so as to follow a vertical location of the swivel axis of the irradiation nozzle with respect to the support. The irradiation nozzle can be configured to rotate about a swivel axis at the horizontal input.

In one or more exemplary embodiments of the disclosed subject matter, a beam transport assembly for conveying a particle beam comprises a beam tube and at least one first bending magnet. The beam tube can have an interior volume maintained under vacuum and can be formed of a material or have a thickness that allows the particle beam to pass through a wall thereof. The at least one first bending magnet can redirect the particle beam from a direction parallel to an axis of the beam tube to an input of an irradiation nozzle. The at least one first bending magnet can be configured to move along the beam tube in the direction parallel to the axis of the beam tube.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

According to one or more embodiments of the disclosed subject matter, a particle therapy system can have an irradiation nozzle that is configured to move along a substantially linear path (e.g., in a vertical direction). A beam transport system between the beam source (e.g., a particle accelerator) and the irradiation nozzle can be designed to accommodate the linear motion of the irradiation nozzle. The substantially linear motion of the irradiation nozzle of the disclosed particle therapy system allows for a reduced footprint as compared to traditional particle therapy systems employing a rotating gantry.

Figure 1A:
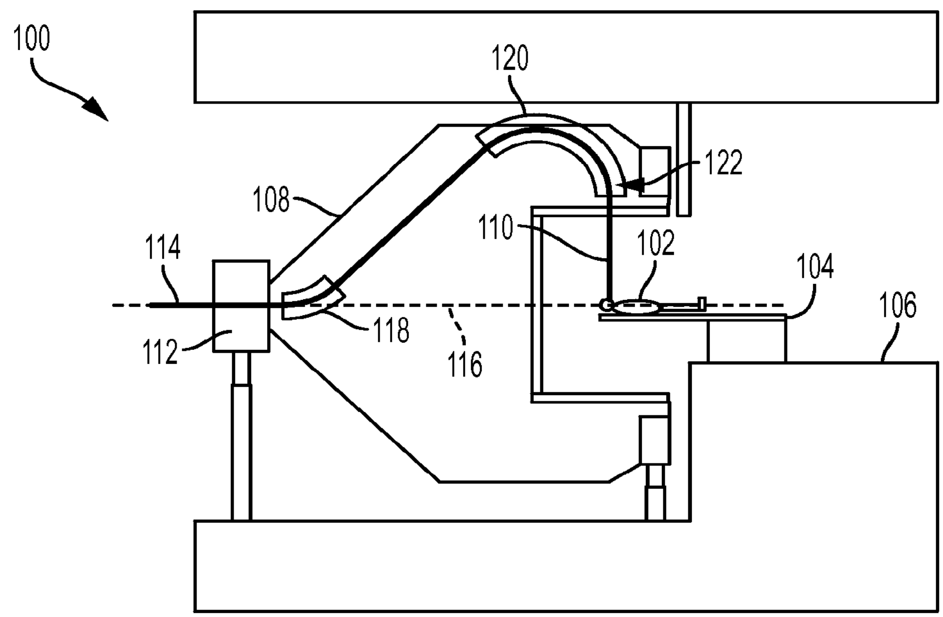
FIG. 1A shows a simplified cross-sectional view of a typical particle therapy system utilizing a rotating gantry.
Figure 1B:
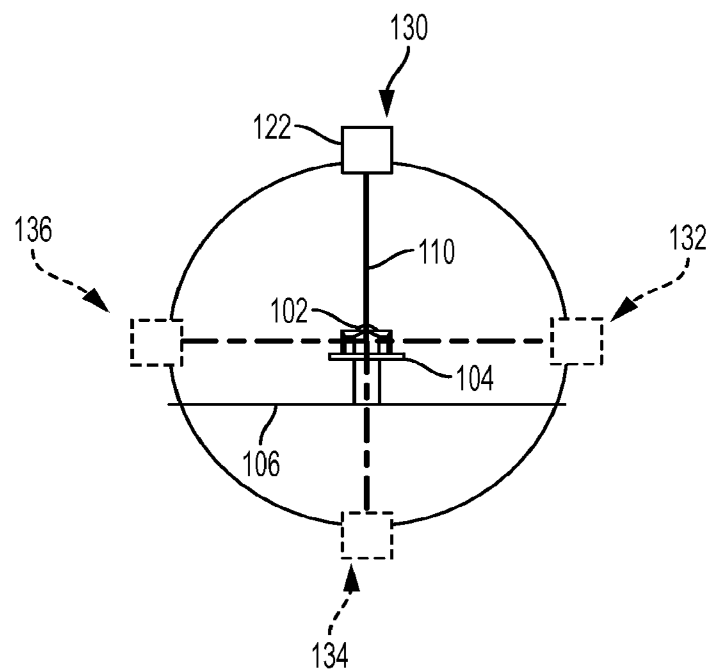
FIG. 1B shows the different positions of the irradiation nozzle as it is rotated around the patient by the gantry.
Figure 2A:
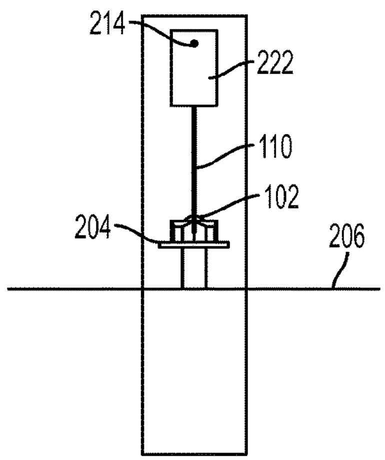
FIGS. 2A-2E show different positions of a nozzle of an irradiation system and of a patient support to provide 360° of irradiation by a particle beam without using a rotating gantry, according to one or more embodiments of the disclosed subject matter.
Figure 2B:
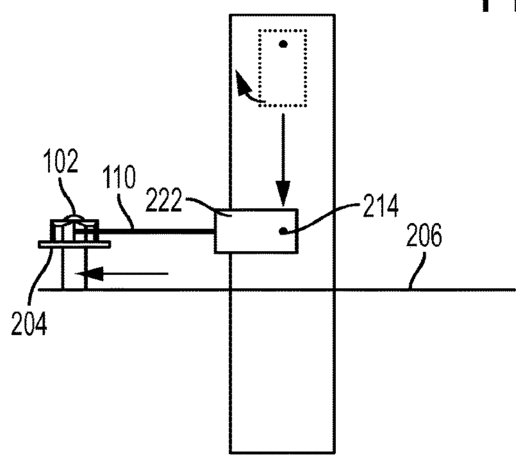
Figure 2C:
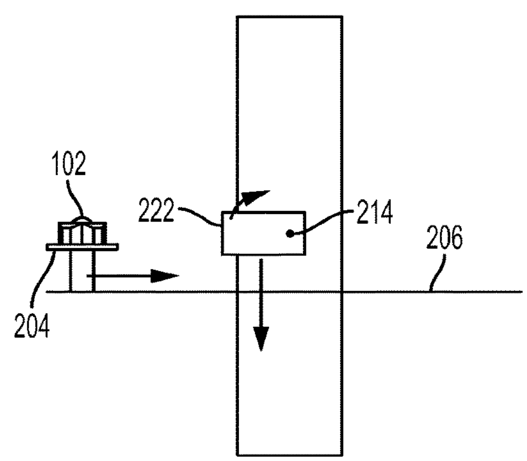
Figure 2D:
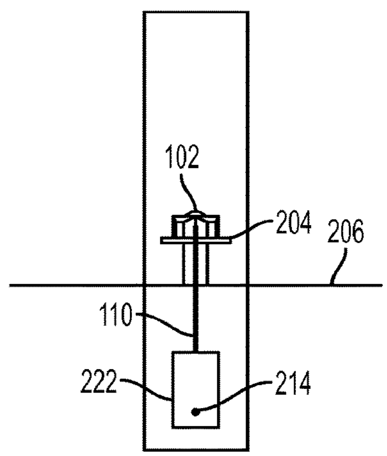

Instead of rotating the irradiation nozzle using a gantry around a patient located at the center of the gantry, embodiments of the disclosed subject matter are able to irradiate the patient through a full 360° of coverage by combining linear motion of the irradiation nozzle (e.g., vertical motion), linear motion of the patient support (e.g., horizontal motion), and/or rotational motion of the irradiation nozzle about an axis spaced from the patient (e.g., at a location where the beam enters the irradiation nozzle). For example, positioning of an exemplary irradiation nozzle 222 about a patient 102 supported on a support 204 is shown in FIGS. 2A-2E. The irradiation nozzle 222 can move in a vertical direction from a maximum vertical height, as shown in FIG. 2A, to a lowest vertical height, as shown in FIG. 2D, which may be below a floor 206. Alternatively, the patient 102 may be positioned by support 204 at a sufficient height above the floor 206 such that the irradiation nozzle 222 can irradiate the patient 102 from underneath without moving below floor 206.

Figure 2E:
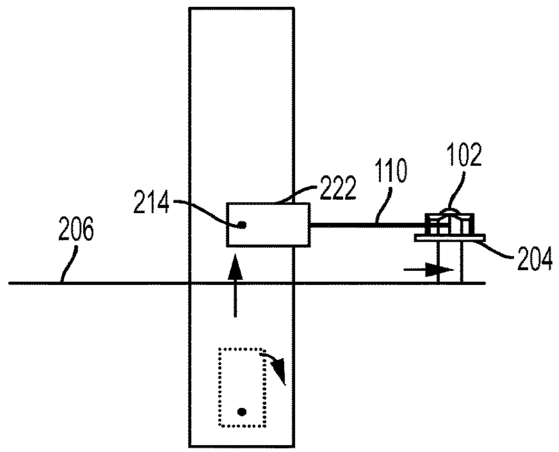

As the irradiation nozzle 222 moves vertically, the irradiation nozzle can rotate about a swivel axis 214 to continue to direct the beam 110 at the patient 102. The support 204 can be configured to move horizontally as the irradiation nozzle 222 displaces so as to maintain a beam path length between the irradiation nozzle 222 and the patient 102. Thus, the irradiation nozzle 222 can move vertically downward from a 0° position, as shown in FIG. 2A, while rotating clockwise about axis 214 and moving support 204 horizontally to the left (i.e., in a plane perpendicular to the swivel axis 214) in order to irradiate the patient 102 from a 90° position, as shown in FIG. 2B. Similarly, the irradiation nozzle 222 can move vertically downward from the 90° position, as shown in FIG. 2C, while rotating clockwise about axis 214 and moving support 204 horizontally to the right (i.e., in a plane perpendicular to the swivel axis 214) to be able to irradiate the patient 102 in an 180° position, as shown in FIG. 2D. To irradiate the patient 102 from a 270° position, as shown in FIG. 2E, the irradiation nozzle 222 can move vertically upward from the 180° position, as shown in FIG. 2D, while rotating clockwise about axis 214 and moving support 204 horizontally to the right. Alternatively, the irradiation nozzle 222 can move vertically downward from the 0° position, as shown in FIG. 2A, while rotating counterclockwise about axis 214 and moving support 204 horizontally to the right (i.e., in a plane perpendicular to the swivel axis 214) in order to irradiate the patient 102 from a 270° position, as shown in FIG. 2E.

To allow for the linear motion of the irradiation nozzle 222, a beam transport assembly can vary a path length for the particle beam, for example, to follow motion of the irradiation nozzle 222. In some embodiments, the variable path length of the particle beam can be provided by an extendable portion of the beam transport assembly. Additionally or alternatively, the variable path length of the particle beam can be provided by moving a deflector (e.g., one or more bending magnets, such as dipole magnets) along a vertical axis of a single beam tube, such that the particle beam exits through a wall of the beam tube with minimal scattering.

The beam transport assembly can have an interior volume under vacuum through which the particle beam travels en route from the source (e.g., the accelerator) to the irradiation nozzle. The vacuum within the interior volume may assist in minimizing or at least reducing the amount of scattering of the particle beam, which may otherwise widen due to scattering if propagating through normal air. The beam transport assembly can accommodate changes in the distance between a particle source and the irradiation nozzle through corresponding changes in the particle beam path length in order to provide a predetermined stroke, for example, at least 300 cm, which allows particle beam to follow the linear movement of the irradiation nozzle.

The beam transport arm or assembly can include one or more first beam control elements, e.g., one or more focusing magnets (e.g., quadrupole magnets), that displace longitudinally with the expandable portion. The beam transport assembly can also include one or more second beam control elements, e.g., one or more steering magnets (i.e., magnets that bend the particle beam in a single plane), which can remain fixed despite movement of the expandable portion in some embodiments or can displace longitudinally with the expandable portion in other embodiments. Alternatively, the one or more first beam control elements can be fixed despite movement of the expandable portion and the one or more second beam control elements can displace longitudinally with the expandable portion. As a result, in some embodiments, the location of the first beam control elements with respect to the second beam control elements can vary as the expandable portion changes from a contracted state to an expanded state. One or more of the beam control elements (e.g., the one or more focusing magnets and/or the one or more steering magnets) can be located outside of a vacuum (e.g., outside of or surrounding a beam tube through which the particle beam passes) or within a vacuum (e.g., within the beam tube through which the particle beam passes).

Embodiments of the disclosed subject matter can provide one or more of the following functions:

(1) controlled movement of the expandable portion, when provided, between contracted and expanded states;

(2) controlled changes in a path length of the particle beam along a beam tube of the beam transport assembly between contracted and expanded lengths;

(3) vacuum maintained within the beam transport assembly despite movement of the beam transport assembly; and (4) control of beam optics to compensate for variations in beam properties due to changes beam path length of the expandable portion and/or passage of the particle beam through a wall of the beam tube of the beam transport assembly.

Figure 3:
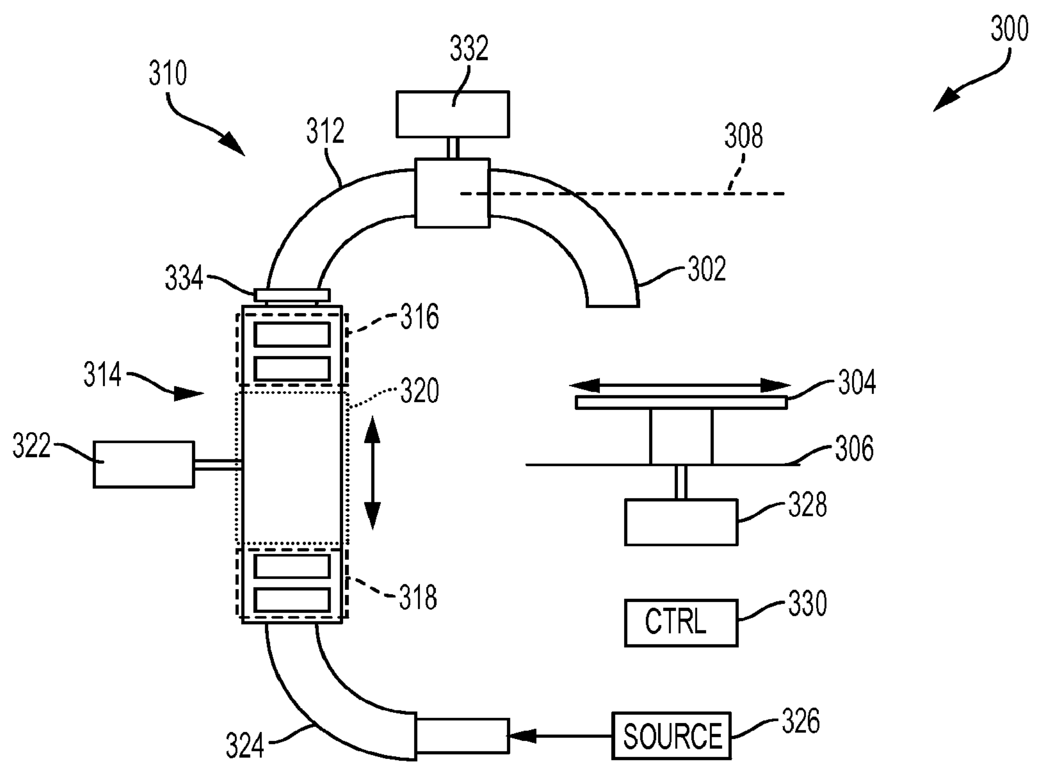
FIG. 3 is a simplified diagram of components of an irradiation system having a beam transport assembly with an expandable portion, according to one or more embodiments of the disclosed subject matter.

FIG. 3 illustrates various components of an exemplary particle therapy system 300 according to one or more embodiments of the disclosed subject matter. The particle therapy system 300 includes an irradiation nozzle 302 and a beam transport assembly 312 that conveys a particle beam from the irradiation source 326. A moveable support 304 can position a patient at an elevation above floor 306 with respect to the irradiation nozzle 302. For example, the support 304 can move horizontally, for example, in a direction parallel to a plane perpendicular to nozzle swivel axis 308, about which irradiation nozzle 302 can rotate. The support 304 may also be configured to move horizontally in a direction parallel to nozzle swivel axis 308 and/or vertically in a direction perpendicular to the floor 306.

The irradiation nozzle 302 can include known beam scattering and/or beam scanning mechanisms in order to achieve an appropriate dose conformation in the patient. The beam, which may be generated by a beam source 326 and guided to the irradiation nozzle 302 by the beam transport assembly 310, enters into the irradiation nozzle along a direction parallel to the nozzle swivel axis 308 (e.g., at a horizontal input of nozzle 302). Within the irradiation nozzle 302, the beam is deflected away from the entrance direction, for example, by 90° such that the beam leaves the irradiation nozzle in a direction perpendicular to the entrance direction. For example, the deflection can be achieved by suitable deflection magnets or other deflection devices.

The irradiation nozzle 302 can be moved at least vertically (i.e., a movement which has at least a vertical translational component toward or away from the floor 306). In addition, the irradiation nozzle 302 can be rotated around a nozzle swivel axis 308. The particle beam may enter the irradiation nozzle 302 from the beam transport assembly 310 along the nozzle swivel axis 308 or at least parallel to the nozzle swivel axis 308. Such a configuration allows the patient to be irradiated from various angular directions by a combination of linear and rotational movement of the irradiation nozzle 302 with horizontal movement of the patient support 304, for example, as described above with respect to FIGS. 2A-2E. As a result, the irradiation with the disclosed particle therapy system can avoid a vertical movement of the irradiation object, e.g., the patient, while irradiating it from all angular directions.

The nozzle swivel axis 308 can be substantially horizontal, for example, parallel to a floor 306. Such a configuration may provide for a more simple design of the irradiation device, in particular, in combination with deflection of the beam within the irradiation nozzle 302 by 90°. If the nozzle swivel axis 308 is horizontal and the beam is deflected within the irradiation nozzle 302 by 90°, the plane in which the particle beam travels during motion of the irradiation nozzle 302 is substantially vertical.

The beam transport assembly 310 of the particle therapy system 300 can further include an expandable portion 314 that can change a length of a beam pathway 320 between a first set of beam control optics 316 (e.g., focusing magnets) and a second set of beam control optics 318 (e.g., focusing magnets). The expandable portion 314 can thus enable the beam transport assembly 310 to follow and/or cause the vertical motion of the irradiation nozzle 302. The beam transport assembly 310 can also include one or more first deflectors 324 (e.g., bending magnets) to deflect the particle beam from the source 326 to the expandable portion 314 and one or more second deflectors 312 (e.g., bending magnets) to deflect the particle beam from the expandable portion 314 to the irradiation nozzle 302.

The vertical movement of the irradiation nozzle 302 can be caused by an expansion/contraction of the expandable portion 314 of the beam transport assembly 310. Alternatively, a separate mechanism can move the irradiation nozzle 302 and/or deflector 312, and the expandable portion 314 can be configured to follow the motion of the irradiation nozzle 302 and/or the deflector 312. For example, the beam transport assembly 310 and the expandable portion 314 can be arranged substantially vertical, and the nozzle swivel axis 308 can be substantially horizontal. For example, the beam can enter from the source 326 into the beam transport assembly 310 in a substantially horizontal direction and can deflected, e.g., by deflector 324, into a substantially vertically arranged expandable portion 314 with a further deflector 312 at an end thereof.

A control system 330 can be provided for controlling various aspects of the particle therapy system 300, in particular, the movements of the irradiation nozzle 302, for example, the rotation and vertical displacement of the irradiation nozzle 302 to enable 360° of irradiation coverage of the irradiation object. Optionally, the control system 330 may also control the lateral position and the angular direction of the particle beam irradiated from the irradiation nozzle 302. Optionally, the control system 330 can include position verification systems configured to verify the position of the irradiation object (i.e., the patient) and to generate control signals for controlling the movement of the support 304 and the nozzle 302 responsively thereto.

Additionally, the control system 330 can be configured to coordinate at least two of three movements of components of the particle therapy system 300, for example, (i) horizontal movement of the patient support 304, (ii) vertical movement of the irradiation nozzle 302 (and optionally any associated vertical movement of the expandable portion of beam transport assembly 310 and/or change in beam path length through the beam transport assembly to accommodate movement of the irradiation nozzle 302), and (iii) rotational movement of the irradiation nozzle 302 about swivel axis 308 such that the particle beam continues to impinge on the patient as the support 304 and/or irradiation nozzle 302 are moved. The horizontal movement of the support 304 and the vertical and rotational movements of the irradiation nozzle 304 are coordinated such that the particle beam impinges on the patient at a predetermined distance (e.g., a constant radius) from the irradiation nozzle 302 as the support 304 and/or the nozzle 302 are moved, thereby allowing irradiation from different angular directions but at a constant or pre-determined distance from the irradiation nozzle 302. For example, the control system 330 can control a drive system 328 that moves the patient support 304, a rotational drive 332 that rotates the irradiation nozzle 302, and/or a vertical drive 322 that displaces the expandable portion 314. For example, the vertical drive 322 can be a screw drive, a hydraulic or pneumatic piston drive, or any other drive capable of providing controlled vertical displacement.

Optionally, the support 304 for the irradiation object can be moved vertically, either by moving the support 304 relative to the room floor 306, or by elevating and lowering the room floor 306 with the support 304 placed thereon. The vertical movement of the support 304 may be combined with a horizontal movement of the support 304 and/or a rotational movement of the support 304 around a vertical axis (not shown) and/or a vertical and/or rotational movement of the irradiation nozzle 302 about the nozzle swivel axis 308. A suitable combination of such movements may be used, for example, for advantageous irradiation treatment plans and/or for avoidance of collisions between the nozzle 302 and the irradiation object or support 304.

Since the optic properties of the beam transport assembly 310 may be altered as the length of the expandable portion 314 changes, the control unit 330 can control the beam control optics (e.g., the first set of optics 316 and/or the second set of optics 318) responsively to changes in the length of the expandable portion 314 of the beam transport assembly 310. For example, control unit 330 can change the strength of one or more of the first and second focusing magnets to compensate for changes in the distance between the first and second focusing magnets and/or the changed length of beam tube 320 in order to maintain a profile of the particle beam despite the changed length of the expandable portion. The control unit may change the strength of the focusing magnets as a function of the position of the irradiation nozzle 302, for example, using a lookup table or through the use of feedback, for example, from a sensor 334 arranged along the beam transport assembly 310 (e.g., a telescoping beam transport arm) or the beam irradiation nozzle 302 and configured to detect one or more characteristics of the particle beam.

Figure 4:
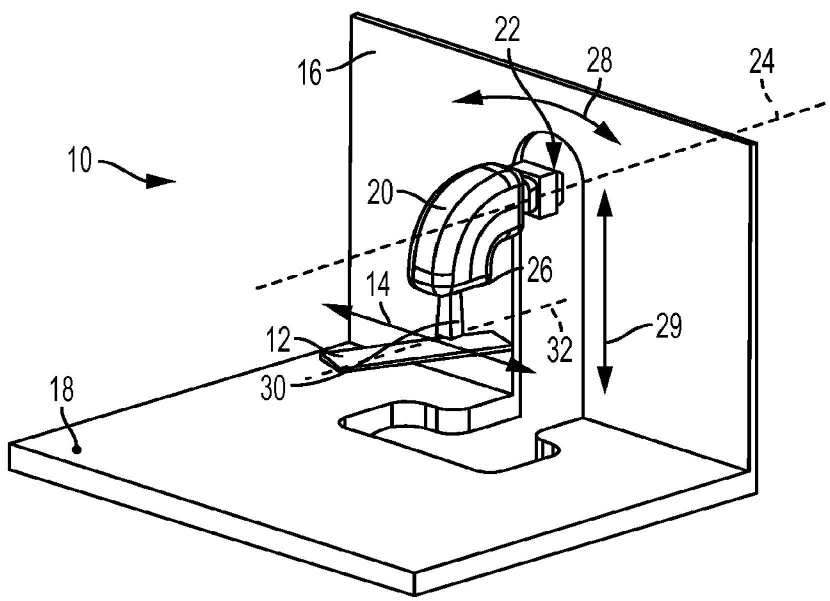
FIG. 4 shows a perspective view of an irradiation system, according to one or more embodiments of the disclosed subject matter.

FIGS. 4-10 show various views of a particle therapy system as an irradiation nozzle moves around a patient. FIG. 4 shows a perspective view of a particle therapy system 10, which includes a support 12 for the irradiation object, for example, a patient support as part of administering a particle therapy. As indicated by arrow 14, the support 12 can be moved left and right in a horizontal direction, which can be parallel to a back wall 16 and floor 18 of the room in which the irradiation object is located, i.e., the treatment room in case of particle therapy.

The particle therapy system 10 further comprises an irradiation nozzle 20 that directs a charged particle beam 30, for example a proton beam, toward the support 12 for the irradiation object. The particle beam can enter the irradiation nozzle 20 at an entrance side 22 thereof in a substantially horizontal direction, for example, along the horizontal nozzle swivel axis 24, or at least substantially parallel to the nozzle swivel axis 24. Within the irradiation nozzle 20, the particle beam 30 can be deflected by 90° so as to exit from the irradiation nozzle 20 at an exit side 26 thereof in a direction substantially perpendicular to the nozzle swivel axis 24. As indicated by arrow 28, the nozzle 20 can be rotated around the nozzle swivel axis 24. Additionally, the nozzle 20 can be moved vertically such that the nozzle swivel axis 24 can be raised and lowered as indicated by arrow 29. When the nozzle 20 is rotated around the nozzle swivel axis 24, the beam exiting from the irradiation nozzle 20 remains within a substantially vertical plane.

As shown in FIGS. 5-9, the combination of rotation about the nozzle swivel axis 24 and vertical displacement of the irradiation nozzle 20 allows irradiation of the irradiation object 13 (e.g., a patient in the case of a particle therapy) from all angular directions. The irradiation nozzle 20 can be rotated around its nozzle swivel axis 24 to angular positions between −180° and +180° (i.e., 360° of coverage in a plane perpendicular to the swivel axis 24). Additionally, the irradiation nozzle 20 can be moved vertically from positions above the support 12 to positions below the support 12. The support can be moved horizontally, parallel to the back wall 16 of the room, to the left or right with respect to the vertical path of the nozzle swivel axis 24. This allows side positions of the nozzle 20 with respect to the irradiation object 13 such that the nozzle 20 can pass the support 12 as it travels on its vertical path.

Figure 5:
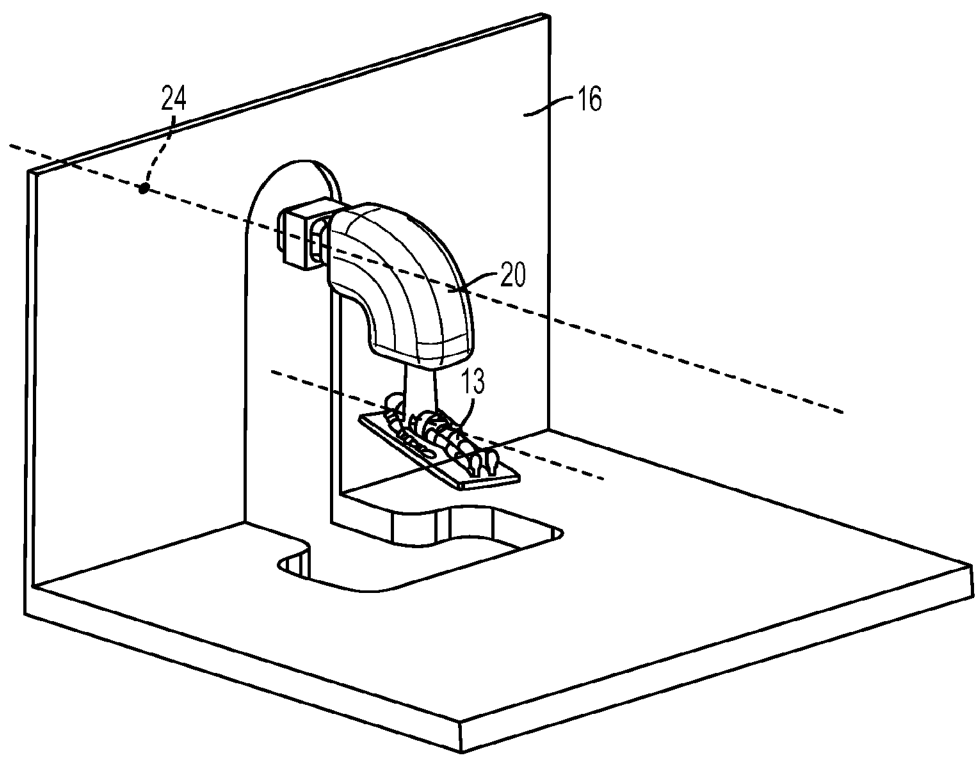
FIG. 5-9 show perspective views of the irradiation system of FIG. 4 in 0°, 45°, 90°, 180°, and 315° positions, respectively, according to one or more embodiments of the disclosed subject matter.
Figure 6:
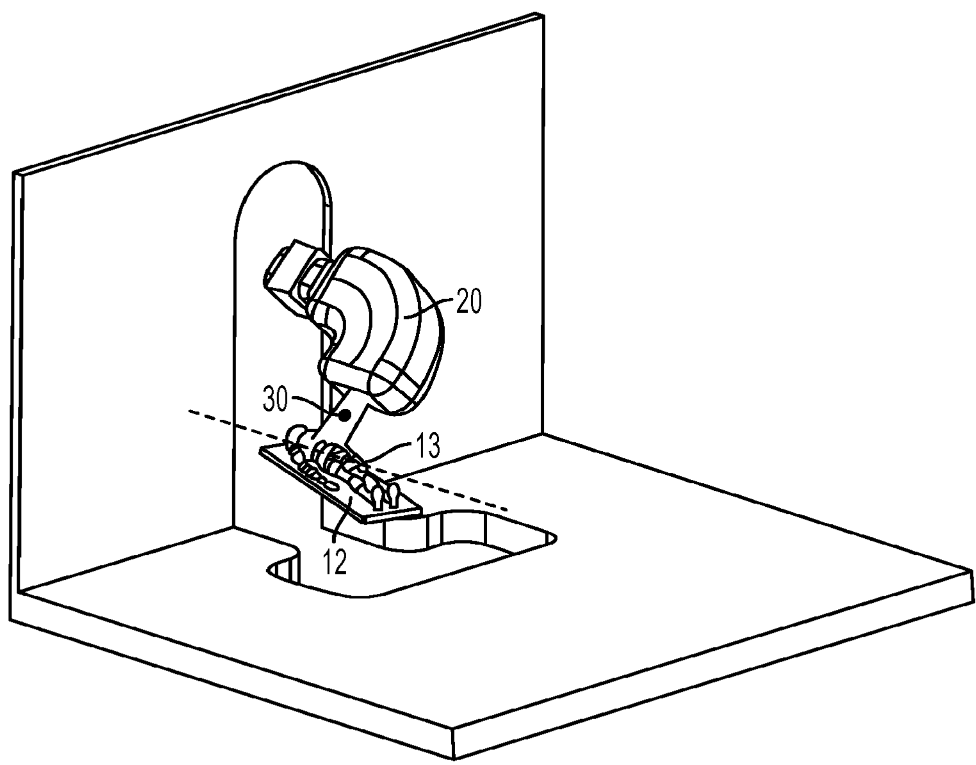
Figure 7:
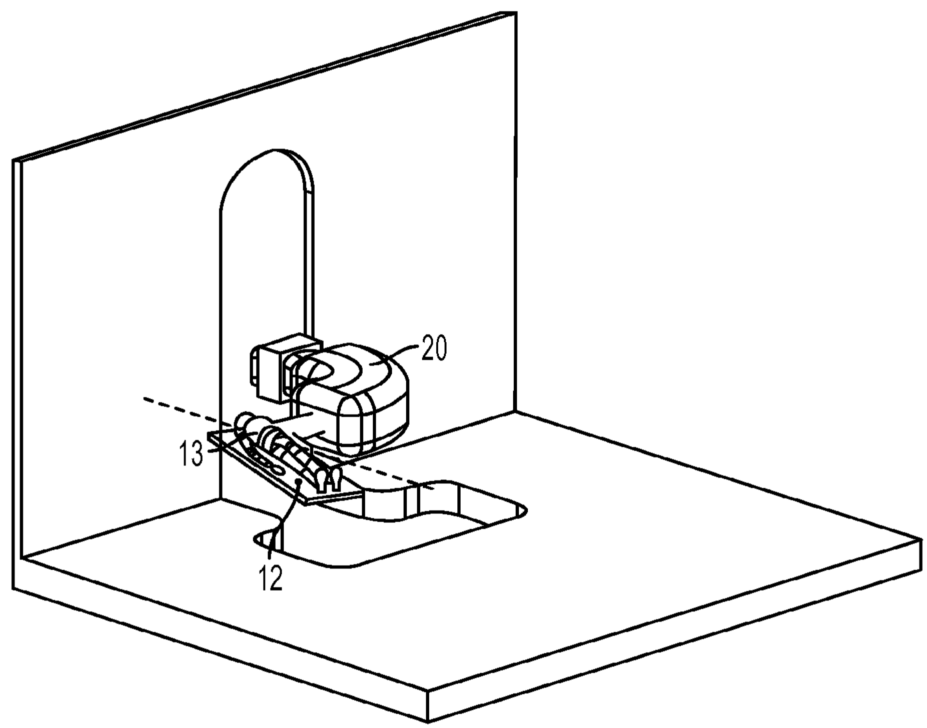
Figure 8:
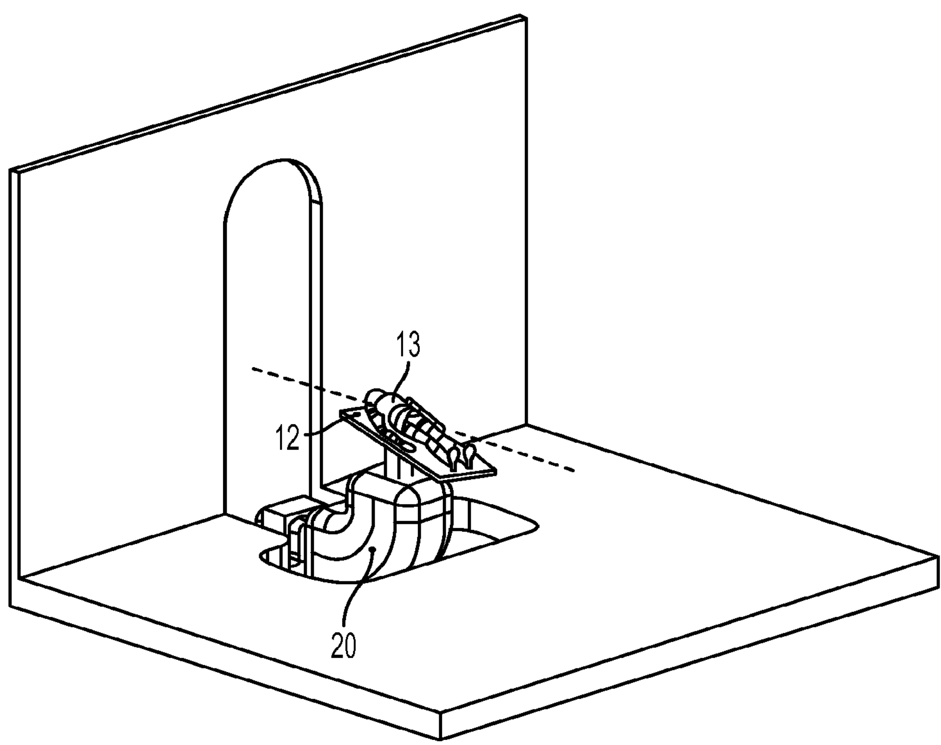
Figure 9:
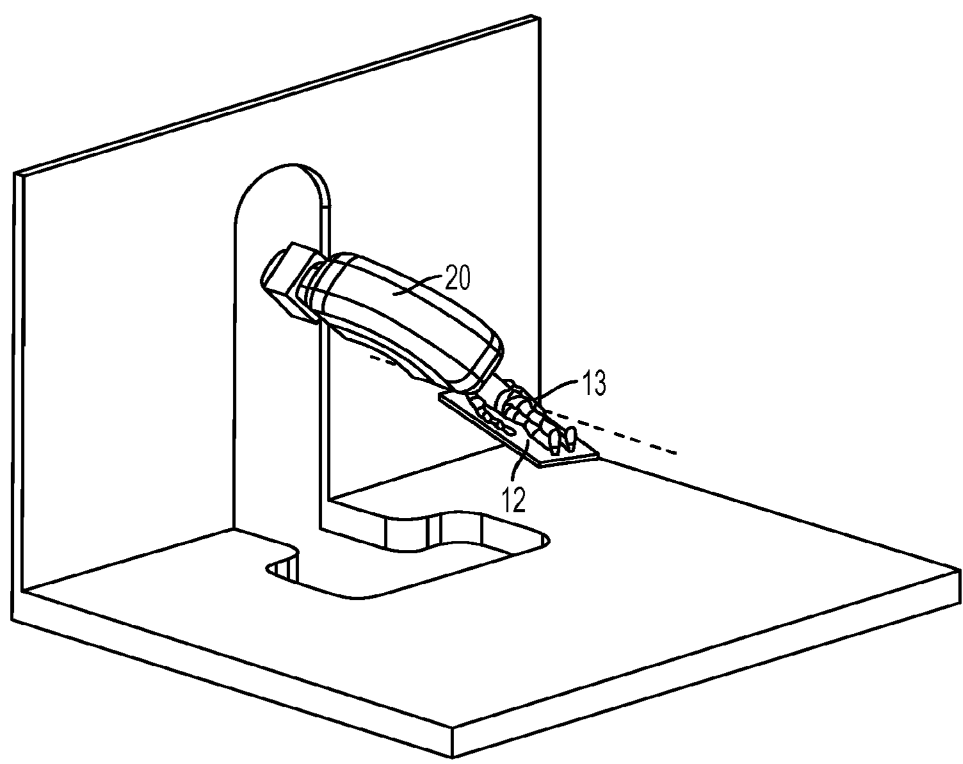

Thus, in FIG. 5, the irradiation object 13 can be irradiated from directly above, which is a 0° position. As shown in FIG. 6, the support 12 with the irradiation object 13 can be moved to the left as the irradiation nozzle 20 moves down in the vertical direction and is rotated clockwise around swivel axis 24 to a 45° position. The horizontal movement of the support 12 and the vertical and rotational movements of the nozzle 20 can be coordinated such that the particle beam 30 impinges onto the irradiation object 13 at a same distance from the irradiation nozzle 20 as when in 0° position, but from an angular direction of 45° with respect to the 0° position. As shown in FIG. 7, the support 12 can be moved further to the left as the irradiation nozzle 20 is moved lower and rotated further in the clock-wise direction around its swivel axis 24 such that the irradiation object 13 is irradiated from a horizontal direction (i.e., 90° position) but at the same distance from the irradiation nozzle as in the 0° and 45° positions. As shown in FIG. 8, the support 12 can be moved back to the central position on the vertical path of the irradiation nozzle 20 while the irradiation nozzle 20 is moved downward to a lower position (e.g., a lowermost vertical position that may be at or below floor 18 of the treatment room) and rotated such that the beam irradiates the object 13 from directly below, i.e., a 180° position. When moving into the 180° position of FIG. 8, the movements of the support 12 and the irradiation nozzle 20 are coordinated such that the irradiation object 13 is irradiated at the same distance from the nozzle 20 as in the irradiation positions of FIGS. 5-7. As shown in FIG. 9, the support 12 can be moved in a direction opposite to that of FIG. 6, i.e., to the right from the vertical path of the irradiation nozzle 20, while the irradiation nozzle 20 is moved to the same vertical position as in FIG. 6, but rotated counter-clockwise to a −45° position. In the arrangement shown in FIG. 9, the irradiation object 13 is irradiated from an angular direction of −45° as compared to the vertical direction, but at the same distance from the irradiation nozzle 20 as in the irradiation positions of FIG. 5-8.

Figure 10:
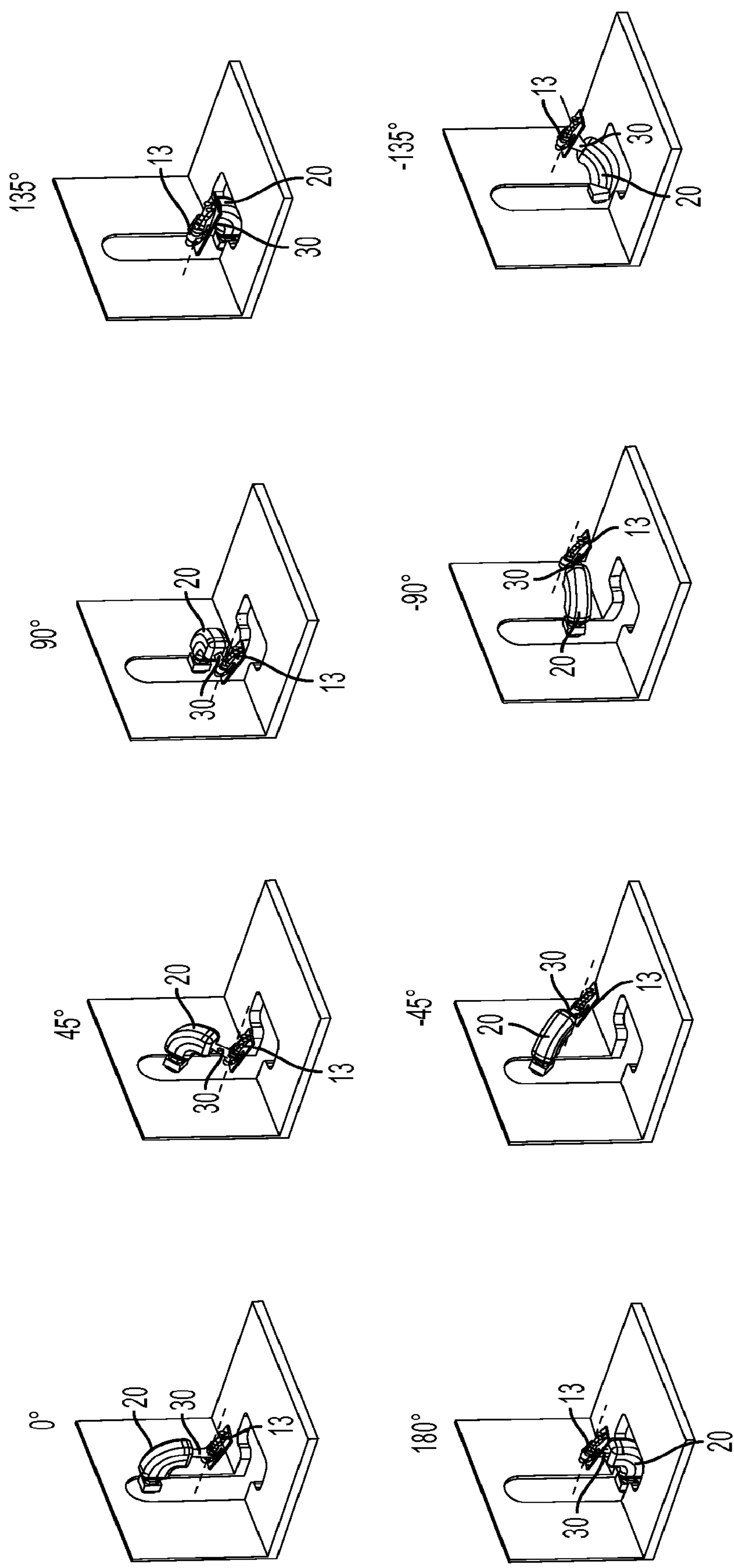
FIG. 10 shows perspective views of the irradiation system of FIG. 4 in a sequence of irradiation from various angular directions between ±180°, according to one or more embodiments of the disclosed subject matter.

FIG. 10 shows an overview of the sequence of irradiation positions 0°, 45°, 90°, 135°, 180°, −45°, −90° and −135°. By suitable movement of the support 12 and the irradiation nozzle 20, the irradiation object 13 can be irradiated from all angular directions at a constant distance from the irradiation nozzle 20. Moreover, by moving the support 12 along its length (e.g., along dashed line 32 illustrated in FIG. 4, which is parallel to the swivel axis 24) the point where the beam from irradiation nozzle 20 impacts the irradiation object 13 can be shifted to allow different portions of the object 13 to be irradiated.

In one or more embodiments of the disclosed subject matter, an exemplary irradiation method can comprise placing an irradiation object (e.g., a patient) onto a support which can move at least horizontally. The method further comprises irradiating a charged particle beam, e.g., a proton beam, from an irradiation nozzle toward the irradiation object. The beam, which may be generated by a beam source (e.g., a particle accelerator) and guided to the irradiation nozzle by a beam transport assembly, is fed into the irradiation nozzle and deflected therein. The angular direction of the beam impinging on the irradiation object can be varied by moving the support and by moving the irradiation nozzle vertically while rotating it around a nozzle swivel axis. The distance from the irradiation nozzle to the irradiation object can be maintained constant or to a pre-determined value while the angular direction of the beam impinging onto the irradiation object can be changed.

Figure 11:
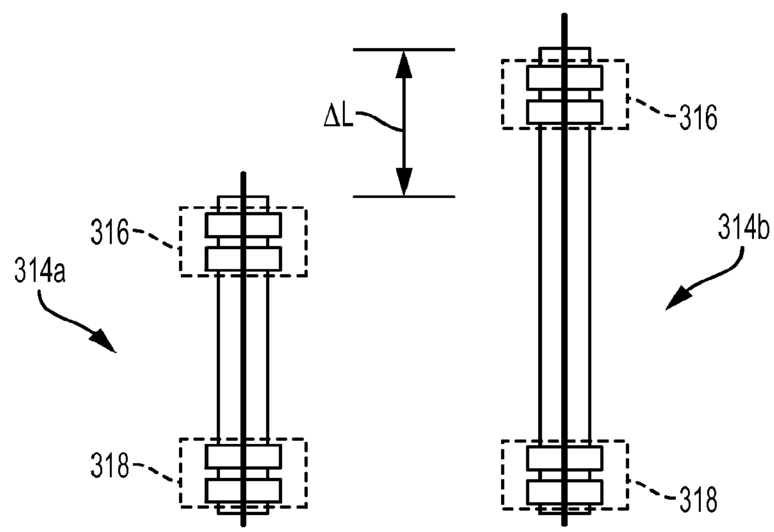
FIG. 11 is a simplified diagram of an expandable portion of a beam transport assembly, according to one or more embodiments of the disclosed subject matter.

As noted above, the linear displacement (e.g., in the vertical direction) of the irradiation nozzle can be achieved via extension or contraction of an expandable portion of the beam transport assembly. As shown in FIG. 11, the beam transport assembly can transition from a contracted state 314*a* having a minimum length to an expanded state 314 having a maximum length in order to provide a desired stroke, ΔL, that corresponds to the desired linear movement of the irradiation nozzle. During the movement of the beam transport assembly 314, the first set of beam control components 316 may be moved with respect to the second set of beam control components 318. For example, the second set of beam control components 318 may be disposed closer to the particle source 326 than the first set of beam control components 318. As a result, the second set of beam control components 318 may remain stationary while the first set of beam control components 318 move with the beam path 320. Alternatively, either or both of the first set of beam control components 316 and second set of beam control components 318 may move with the beam tube 320. The first and second sets of beam control components can have one or more magnets (or other beam components) that can remain fixed with respect to other components within the respective set.

Figure 12:
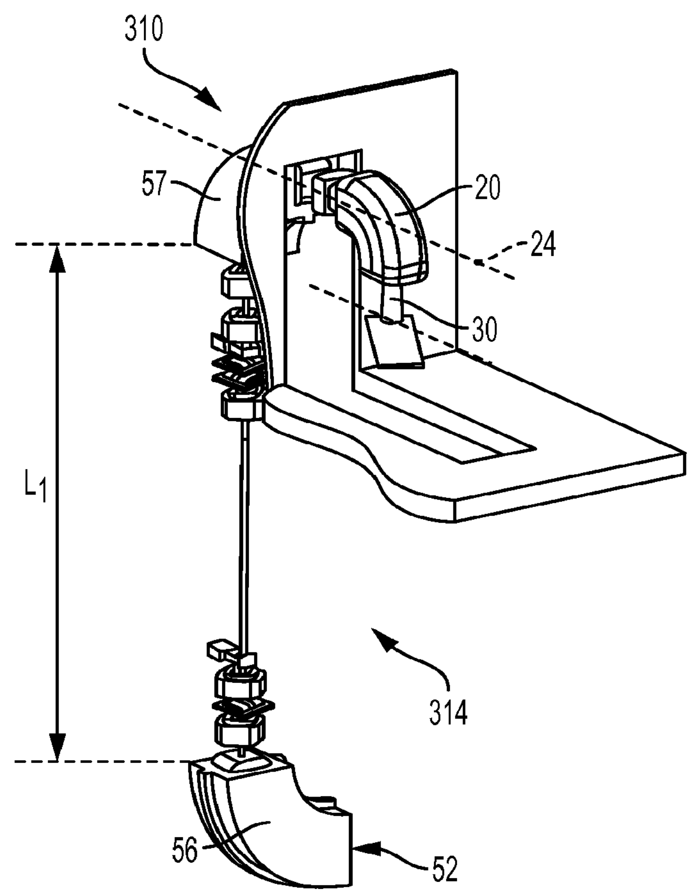
FIG. 12 is a simplified diagram of an irradiation system having a beam transport assembly with an expandable portion in an expanded configuration, according to one or more embodiments of the disclosed subject matter.
Figure 14:
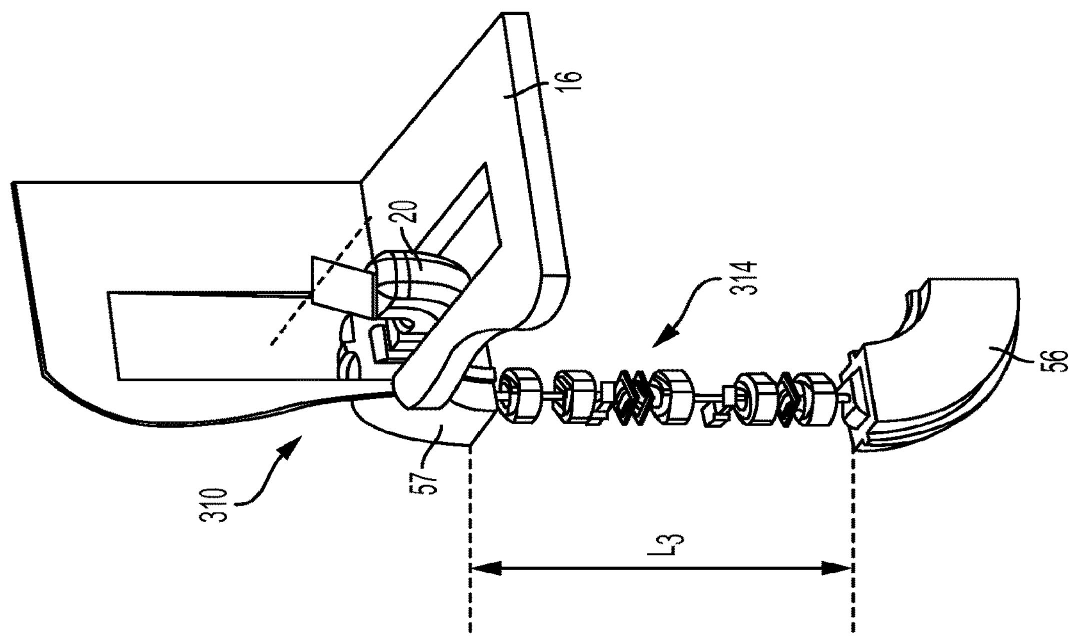
FIG. 14 is a simplified diagram of the irradiation system of FIG. 12 with expandable portion in a contracted configuration.
Figure 13:
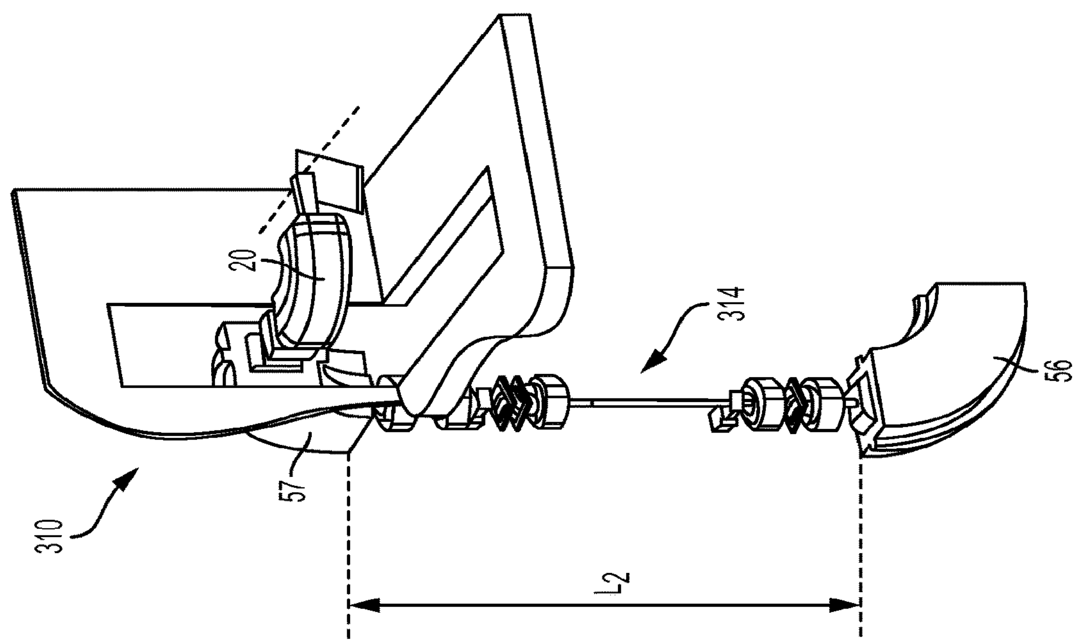
FIG. 13 is a simplified diagram of the irradiation system of FIG. 12 with the expandable portion in an intermediate configuration.
Figure 15A:
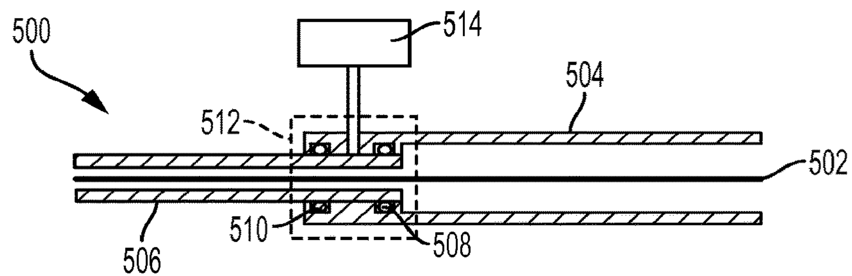
FIGS. 15A-15B show simplified cross-sectional and side views, respectively, of a beam transport assembly expandable portion using a sliding seal, according to one or more embodiments of the disclosed subject matter.
Figure 15B:
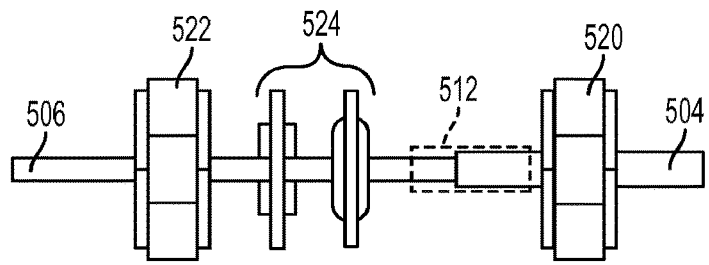

FIGS. 12-14 illustrate vertical movements of an irradiation nozzle 20 by expansion/contraction of an expandable portion 314 of a beam transport assembly 310. The beam transport assembly 310 can include a first deflector 56, which deflects the particle beam (e.g., by 90°) into the vertical expandable portion 314, and a second deflector 57 that deflects the particle beam (e.g., by 90°) into the irradiation nozzle 20. The expandable portion 314 can change length from a maximum length, $L_1$, (i.e., the expanded state) as shown in FIG. 12 to a minimum length, $L_3$, (i.e., the contracted state) as shown in FIG. 14. As noted above, the support 12 can be moved in a horizontal direction in coordination with movement of the irradiation nozzle such that the irradiation object on the support 12 can be irradiated from all angular directions are a predetermined constant distance.

In one or more embodiments, the expandable portion of the beam transport assembly can comprise a telescoping section employing a sliding seal. For example, FIGS. 15A-16C illustrate an exemplary embodiment of an expandable portion of a beam transport assembly with a telescoping section. The telescoping section 500 can include an outer beam tube 504 having a first inner diameter and an inner beam tube 506 having a second outer diameter smaller than the first inner diameter. The inner beam tube 506 can be arranged with an end portion thereof disposed within an interior of the outer beam tube 504 such that the inner beam tube 506 and the outer beam tube 504 can move with respect to each other. For example, the respective axes of the beam tubes 504, 506 may be aligned, and the beam tubes 504, 506 can be constructed to displace axially with respect to each other such that the axial length of the end portion of the inner beam tube 506 accommodated within the outer beam tube 504 is increased or decreased. The particle beam 502 can pass through the interior volume of the beam tubes 504, 506 en route to the irradiation nozzle (not shown) and can be aligned, for example, with respective axes of the beam tubes 504, 506.

The interior volume of the beam tubes 504, 506 can be maintained under vacuum so that scattering of the particle beam within the beam tubes 504, 506 can be minimized or at least reduced. The vacuum can be maintained using one or more seals arranged between the inner beam tube 506 and the outer beam tube 504. For example, a first sliding seal 508 and/or a second sliding seal 510 can be provided between an outer circumferential surface of the inner beam tube 506 and an inner circumferential surface of the outer beam tube 504 in an overlapping region 512. As the beam tubes 504, 506 are axially spaced from each other, the seals 508, 510 can be constructed to slide on one or more of the circumferential surfaces to prevent the vacuum within the beam tubes 504, 506 from being compromised. Optionally, a differential pump 514 can be provided between the seals 508, 510 in the overlapping region 512 in order to provide a transition between the vacuum environment within the beam tubes and the atmosphere external to the beam tubes.

The beam tubes 504, 506 are sized to provide sufficient variation in beam path length (i.e., stroke of the expandable section) to accommodate the desired movement of the irradiation head, for example, at least 300 cm. For example, the minimum axial dimension of the telescoping section 500 (e.g., in the contracted state) can be equal to the maximum desired stroke length and the maximum axial dimension of the telescoping section 500 (e.g., in the expanded state) can be equal to twice the maximum stroke length.

Figure 16A:
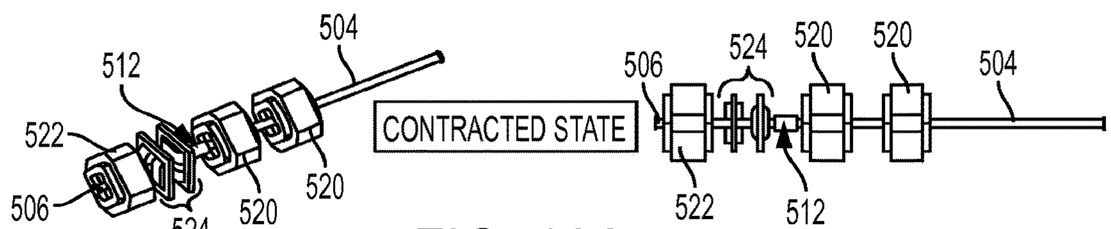
FIG. 16A shows perspective (left) and side (right) views of the expandable portion of FIG. 15B in a contracted state.
Figure 16B:
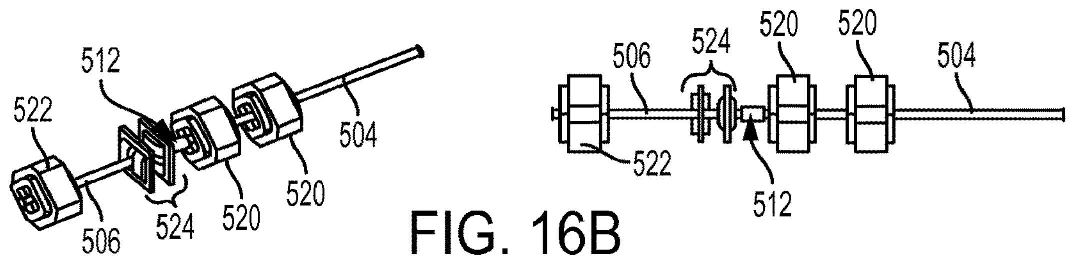
FIG. 16B shows perspective (left) and side (right) views of the expandable portion of FIG. 15B in an intermediate state.
Figure 16C:
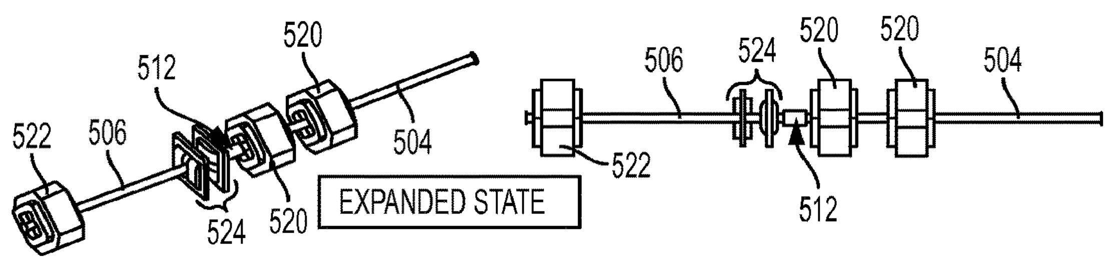
FIG. 16C shows perspective (left) and side (right) views of the expandable portion of FIG. 15B in an expanded state.

Each beam tube 504, 506 can include one or more beam control components coupled thereto so as to be displaced with the respective beam tube. For example, inner beam tube 506 can have one or more focusing magnets 522, e.g., a quadrupole magnet, coupled thereto and capable of being axially displaced with the tube 506, while outer beam tube 504 can have one or more focusing magnets 520, e.g., a quadrupole magnet, coupled thereto. FIGS. 16A-16C illustrate the arrangement of various components as the telescoping section 500 transitions from a contracted state (FIG. 16A) to an intermediate state (FIG. 16B) to a fully expanded state (FIG. 16C). As the inner beam tube 506 moves into the outer beam tube 504, the distance of focusing magnet 522 from focusing magnet 520 is reduced. Conversely, as the inner beam tube 506 withdraws from the outer beam tube 504, the distance of focusing magnet 522 from focusing magnet 520 increases. The magnetic fields of focusing magnet 520 and/or focusing magnet 522 may be controlled (e.g., by the control system 330 of FIG. 3) to compensate for the variations in beam path length and changes in positions of the focusing magnets to maintain a profile of the particle beam.

Alternatively or additionally, other beam control components may be provided with respect to the beam tubes 504, 506 that remain fixed in place despite movement of the beam tubes 504, 506. For example, one or more beam control components 524, such as steering magnets (e.g., dipole magnets), can be arranged about the inner beam tube 506 between the focusing magnet 506 and the overlapping region 512 where the sliding seals are located. As illustrated in FIGS. 16A-16C, the position of the beam control components 524 remains fixed with respect to the sliding seal housing 512 and focusing magnets 520 despite the axial displacement of the inner beam tube 506 and the corresponding displacement of focusing magnet 522. In other contemplated embodiments, the one or more beam control components 524 can be coupled to the inner beam tube 506 so as to move with the beam tube 506 in the same manner as focusing magnet 522.

In one or more embodiments, the expandable portion of the beam transport assembly can comprise a variable length vacuum vessel with a pair of rotating seals. For example, FIGS. 17A-18C illustrate an exemplary embodiment of an expandable portion 700 of a beam transport assembly using a vacuum vessel and a pair of rotating seals. The vacuum vessel 708 has a circumferential surface that varies in height (i.e., a dimension parallel to the propagation direction of particle beam 702). The vacuum vessel 708 can be closed at one axial end by a first rotating seal 710, which interfaces with first beam tube 706. At the other axial end, the vacuum vessel 708 can be closed by a second rotating seal 712, which interfaces with second beam tube 704. Together, the first rotating seal 710, the second rotating seal 712, and the vacuum vessel 708 define an interior volume 714 under vacuum through which the particle beam 702 can travel uninterrupted between the first beam tube 706 and the second beam tube 704.

Figure 17A:
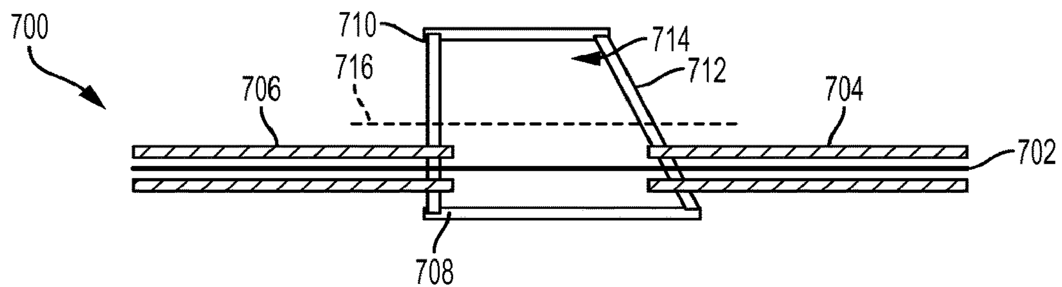
FIGS. 17A-17B show simplified cross-sectional and perspective views, respectively, of a beam transport assembly expandable portion using rotating seals, according to one or more embodiments of the disclosed subject matter.

One or both of the rotating seals 710, 712 can be angled from a plane perpendicular to the propagation direction of the particle beam 702 in order to follow the profile defined by the varying height of the vacuum vessel 708. Alternatively, one of the rotating seals (e.g., first rotating seal 710, as illustrated in FIG. 17A) can be arranged to rotate in a plane perpendicular to the propagation direction of the particle beam 702 while the other of the rotating seals (e.g., second rotating seal 712, as illustrated in FIG. 17A) can be at an angle with respect to said plane. Each of the rotating seals 710, 712 can rotate about a rotation axis 716, which may correspond to a central axis of the vacuum vessel 708. The rotating seals 710, 712 may be coupled together so as to rotate in tandem about axis 716 so as to maintain alignment of the beam path between tubes 704, 706. Alternatively, the rotating seals 710, 712 may be rotated independently about axis 716, but controlled to maintain alignment of the beam path for the particle beam. Alternatively or additionally, the lateral location (i.e., in a direction perpendicular to the direction of beam propagation) of the beam tubes can remain fixed and the relative axial movement of the beam tubes (i.e., parallel to the direction of propagation) causes rotation of the vacuum vessel with respect to the rotating seals to accommodate the change in distance between the beam tubes.

Figure 17B:
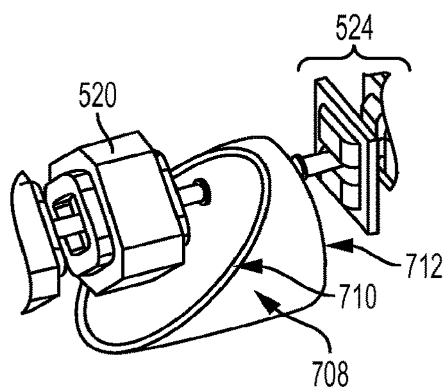
Figure 18A:
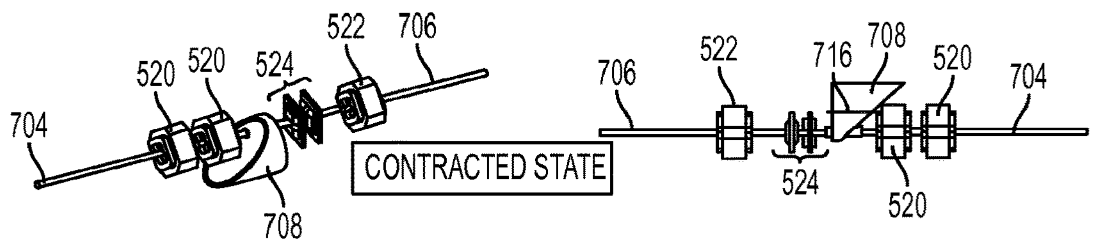
FIG. 18A shows perspective (left) and side (right) views of the expandable portion of FIG. 17B in a contracted state.
Figure 18B:
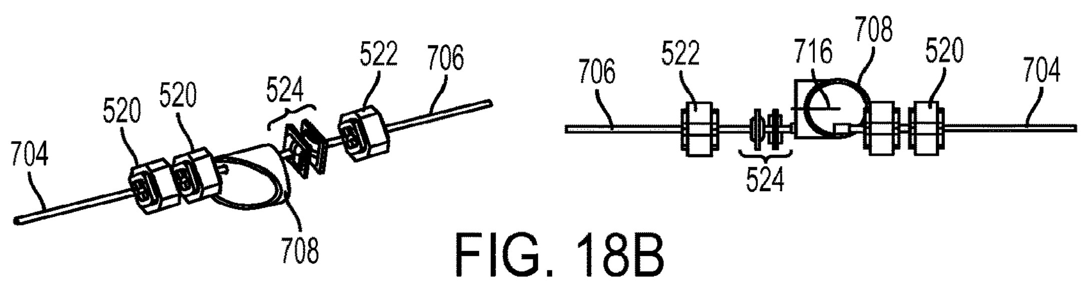
FIG. 18B shows perspective (left) and side (right) views of the expandable portion of FIG. 17B in an intermediate state.
Figure 18C:
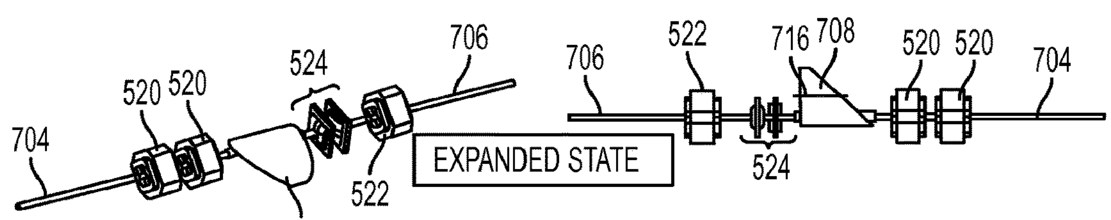
FIG. 18C shows perspective (left) and side (right) views of the expandable portion of FIG. 17B in an expanded state.
Figure 19A:
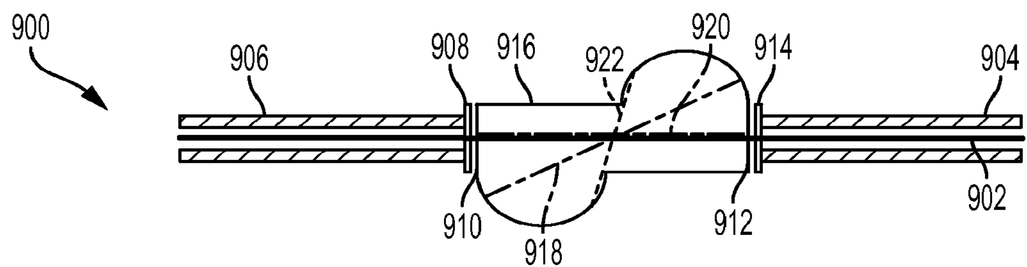
FIGS. 19A-19B show simplified cross-sectional and perspective views, respectively, of a beam transport assembly expandable portion using a rotating vacuum vessel, according to one or more embodiments of the disclosed subject matter.
Figure 19B:
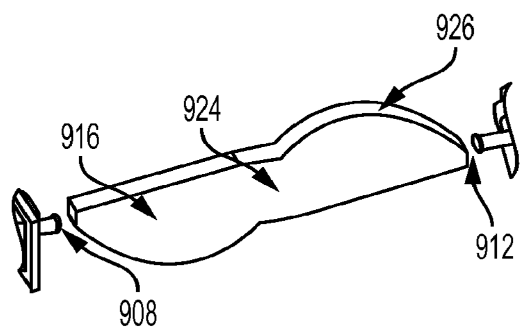

The particle beam 702 travels a distance between the rotating seals 710, 712 that is dictated by the height of the circumferential surface of the vacuum vessel 708. Thus, as the seals 710, 712 rotate about the axis 716, the length of the beam path through the vacuum vessel 708 changes, thereby resulting in expansion or contraction of the expandable portion 700 of the beam transport assembly. FIGS. 18A-18C illustrate the arrangement of various components as the expandable portion 700 transitions from a contracted state (FIG. 18A) to an intermediate state (FIG. 18B) to a fully expanded state (FIG. 18C). When the rotating seals 710, 712 are positioned with the beam tubes 704, 706 proximal to the maximum height of the circumferential surface of the vacuum vessel 708, the expandable portion is in the expanded state, as illustrated in FIG. 17A and FIG. 18C. Conversely, when the rotating seals 710, 712 are positioned with the beam tubes 704, 706 proximal to the minimum height of the circumferential surface of the vacuum vessel 708, the expandable portion is in the contracted state, as illustrated in FIG. 17B and FIG. 18A.

As with the embodiment of FIGS. 15A-16C, the expandable portion 700 of the beam transport assembly can include one or more beam control components coupled thereto so as to be displaced with the respective beam tube (e.g., focusing magnet 522 coupled to tube 706 and focusing magnets 520 coupled to tube 704). The magnetic fields of focusing magnet 520 and/or focusing magnet 522 may be controlled (e.g., by the control system 330 of FIG. 3) to compensate for the variations in beam path length and changes in distance between focusing magnets 520, 522 to maintain a profile of the particle beam.

The position of beam control components on respective sides of the vacuum vessel 708 may be maintained even though the path length for the particle beam 702 may change. In other words, the one or more other beam control components 524 (i.e., between focusing magnet 522 and the vacuum vessel 708) can be configured to move with respective beam tube 706. For example, the relative positions of the focusing magnet 522, the beam control components 524, and/or the rotating seal 710 can be fixed with respect to each other, regardless of whether the expandable portion 700 is in the expanded state or the contracted state. Similarly, the relative positions of the focusing magnets 520 and the rotating seal 712 can be fixed with respect to each other, regardless of whether the expandable portion 700 is in the expanded state or the contracted state. Thus, the change in beam path length caused by rotating seals 710, 712 can be restricted to within the vacuum vessel 708, without affecting the arrangement of beam control components along the respective beam tubes 704, 706.

In one or more embodiments, the expandable portion of the beam transport assembly can comprise a rotating vacuum vessel. For example, FIGS. 19A-20C illustrate an exemplary embodiment of an expandable portion 900 of a beam transport assembly using a rotating vacuum vessel 916 positioned in a gap between a first beam tube 904 and a second beam tube 906. A vacuum window or foil 914 can be positioned at an end of the first beam tube 904 to maintain the vacuum within the tube 904 while allowing particle beam 902 to pass therethrough. Similarly, a vacuum window or foil 908 can be positioned at an end of the second beam tube 906 to maintain the vacuum within the tube 906 while allowing particle beam 902 to pass therethrough.

Vacuum vessel 916 is disposed in the beam path between vacuum window 908 and vacuum window 914 to minimize, or at least reduce, the amount of atmosphere through which particle beam 902 must pass. For example, the particle beam 902 can travel from beam tube 906 through vacuum window 908 into an atmospheric space between vacuum window 908 and vacuum window or foil 910 of the vacuum vessel 916, through vacuum window 910 into the interior volume of the vessel 916 maintained at a vacuum, through vacuum window or foil 912 of the vacuum vessel 916 into an atmospheric space between vacuum window 912 and vacuum window 914, and through vacuum window 914 into the beam tube 904. Alternatively, the atmospheric space between the windows and the vacuum vessel could be eliminated, for example by abutting window 908 against window 910 of the vacuum vessel and by abutting window 914 against window 912 of the vacuum vessel. Thus, the particle beam 902 may pass through at least two, and up to four, different vacuum windows as it travels through the expandable portion.

Figure 20A:
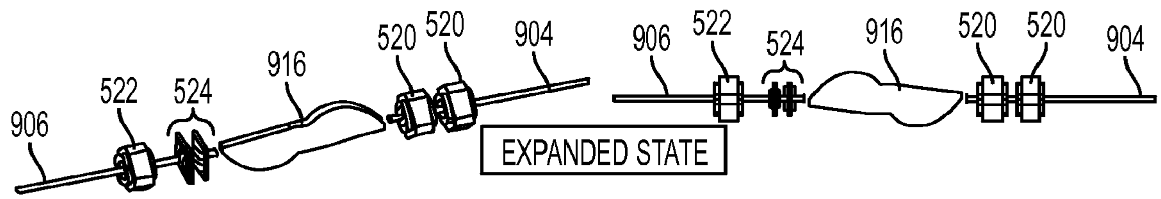
FIG. 20A shows perspective (left) and side (right) views of the expandable portion of FIG. 19B in an expanded state.
Figure 20B:
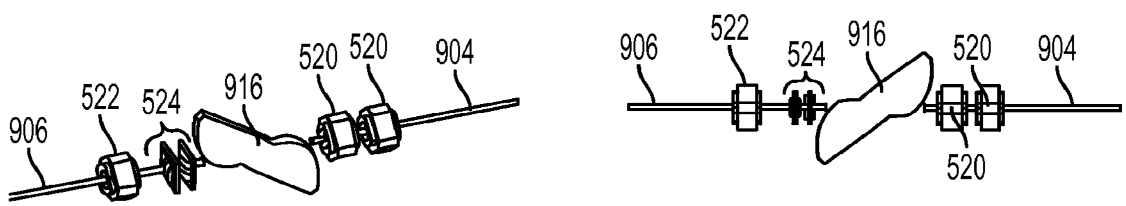
FIG. 20B shows perspective (left) and side (right) views of the expandable portion of FIG. 19B in an intermediate state.
Figure 20C:
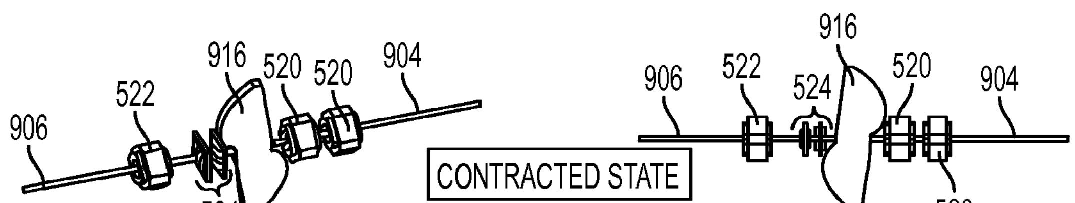
FIG. 20C shows perspective (left) and side (right) views of the expandable portion of FIG. 19B in a contracted state.

As shown in FIGS. 19A-20C, the vacuum vessel 916 can have an undulating non-uniform cross-sectional shape, as viewed in a direction perpendicular to the direction of propagation of the particle beam 902. When the vacuum vessel is rotated about a rotation axis (e.g., central axis 924, which is perpendicular to the beam path of particle beam 902), the distance the particle beam 902 travels through the vacuum vessel 916 changes in a corresponding manner. FIGS. 20A-20C illustrate the arrangement of various components as the expandable portion 900 transitions from an expanded state (FIG. 20A) to an intermediate state (FIG.

20B) to a contracted state (FIG. 20C). As the expandable portion approaches the fully expanded state, a beam path 920 approaching a maximum length through the vacuum vessel 916 is aligned with the particle beam 902. As the expandable portion approaches the fully contracted state, a beam path 922 approaching a minimum length through the vacuum vessel 916 is aligned with the particle beam 902. Intermediate lengths of the expandable portion are accommodated by beam paths within the vacuum vessel 916 that are between the minimum and maximum, for example, beam path 918.

As with the embodiment of FIGS. 17A-18C, the expandable portion 900 of the beam transport assembly can include one or more beam control components coupled thereto so as to be displaced with the respective beam tube (e.g., focusing magnet 522 coupled to tube 906 and focusing magnets 520 coupled to tube 904). The magnetic fields of focusing magnet 520 and/or focusing magnet 522 may be controlled (e.g., by the control system 330 of FIG. 3) to compensate for the variations in beam path length and changes in distance between focusing magnets 520, 522 to maintain a profile of the particle beam. The one or more other beam control components 524 (i.e., between focusing magnet 522 and the vacuum vessel 916) can also be configured to move with respective beam tube, e.g., beam tube 906. For example, the relative positions of the focusing magnet 522, the beam control components 524, and/or the vacuum window 908 can be fixed with respect to each other, regardless of whether the expandable portion 900 is in the expanded state or the contracted state. Similarly, the relative positions of the focusing magnets 520 and the vacuum window 914 can be fixed with respect to each other, regardless of whether the expandable portion 900 is in the expanded state or the contracted state. Thus, the change in beam path length caused by rotating the vacuum vessel 916 can be restricted to the space between window 908 and window 914, without affecting the arrangement of beam components along the respective beam tube 904, 906.

Figure 21A:
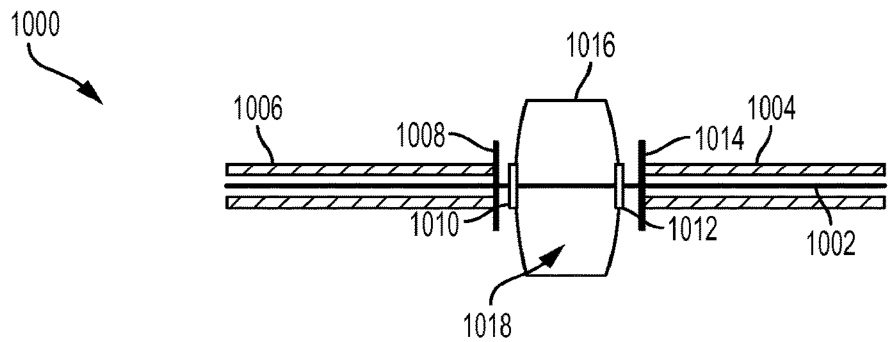
FIGS. 21A-21B show simplified cross-sectional views of a beam transport assembly expandable portion using a gas-filled vessel in a contracted state and in an expanded state, respectively, according to one or more embodiments of the disclosed subject matter.
Figure 21B:
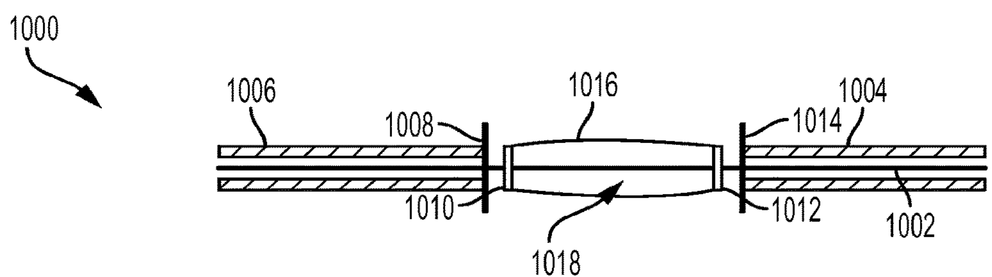

In one or more embodiments, the expandable portion of the beam transport assembly can comprise a gas-filled vessel. For example, FIGS. 21A-21B illustrate an exemplary embodiment of an expandable portion 1000 of a beam transport assembly using a gas-filled vessel positioned in a gap between a first beam tube 1004 and a second beam tube 1006. A vacuum window or foil 1014 can be positioned at an end of the first beam tube 1004 to maintain the vacuum within the tube 1004 while allowing particle beam 1002 to pass therethrough. Similarly, a vacuum window or foil 1008 can be positioned at an end of the second beam tube 1006 to maintain the vacuum within the tube 1006 while allowing particle beam 1002 to pass therethrough.

Vessel 1016 is disposed in the beam path between vacuum windows 1008 and 1014 to minimize, or at least reduce, the amount of external atmosphere through which particle beam 1002 must pass. For example, the particle beam 1002 can travel from beam tube 1006 through vacuum window 1008 into an atmospheric space between vacuum window 1008 and window 1010 of the vessel 1016, through window 1010 into the interior volume of the vessel 1016, through window 1012 of the vessel 1016 into an atmospheric space between window 1012 and vacuum window 1014, and through vacuum window 1014 into the beam tube 1004. Alternatively, the atmospheric space between the windows and the vessel 1016 could be eliminated, for example by abutting window 1008 against window 10110 of the vessel 1016 and by abutting window 1014 against window 1012 of the vessel 1016. Thus, the particle beam 1002 may pass through at least two, and up to four, different windows as it travels through the expandable portion.

An interior volume 1018 of the vessel 1016 can be filled with a gas or gas mixture. Widening of the particle beam caused by scattering can be minimized, or at least reduced, by using certain gases instead of air. Moreover, the use of gas instead of a vacuum avoids vacuum forces acting on the vessel that would otherwise require the vessel to be bulky or made of higher strength material in order to resist such forces. The gas or gas mixture can have an average atomic number that is smaller than that of air. For example, the vessel 1016 can be filled with helium.

The volume expansion of the gas or gas mixture can be altered, for example, by changing the temperature or pressure of the gas. Changes in the volume 1018 of the gas can result in corresponding changes in the path length between windows 1010, 1012 of vessel 1016. For example, the gas-filled vessel 1016 may be formed of a flexible material that can expand or contract depending on the pressure of the gas therein. Alternatively or additionally, the gas-filled vessel 1016 can be formed of a flexible material and can be manipulated to maintain a substantially constant volume despite changes in path length between windows 1010, 1012. For example, the beam path length through the vessel 1016 can be reduced by compressing the vessel 1016 axially (i.e., along a direction of propagation of the particle beam 1002), which results in a corresponding displacement of the volume within the vessel 1016 in a radially outward direction, as illustrated in FIG. 21A. The beam path length through the vessel 1016 can be increased by pulling the vessel 1016 axially (i.e., along a direction of propagation of the particle beam 1002), which pulls the vessel volume in a radially inward direction, as illustrated in FIG. 21B.

As with the embodiment of FIGS. 19A-20C, the expandable portion 1000 of the beam transport assembly can include one or more beam control components coupled thereto so as to be displaced with the respective beam tube (e.g., a focusing magnet coupled to tube 1006 and/or a focusing magnet coupled to tube 1004). The magnetic fields of the focusing magnets may be controlled (e.g., by the control system 330 of FIG. 3) to compensate for any variations in beam path length as well as changes in distance between the focusing magnets to maintain a profile of the particle beam. Changes in beam path length caused by expansion/contraction of the gas-filled vessel 1016 can be restricted to the region between window 1008 and window 1014, without necessarily affecting the relative arrangement of beam components along the respective beam tubes 1004, 1006.

Figure 22A:
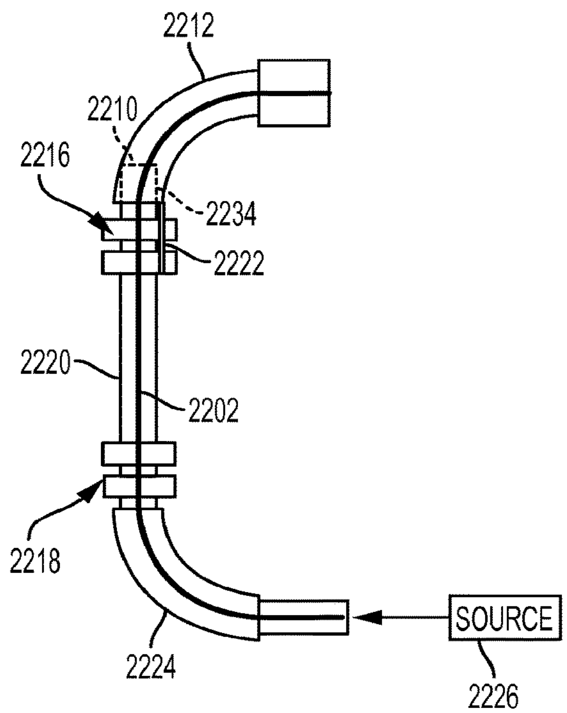
FIGS. 22A-22B are simplified diagrams of components of a beam transport assembly with a single beam tube that accommodates expanded and contracted particle beam path lengths, respectively, according to one or more embodiments of the disclosed subject matter.
Figure 22B:
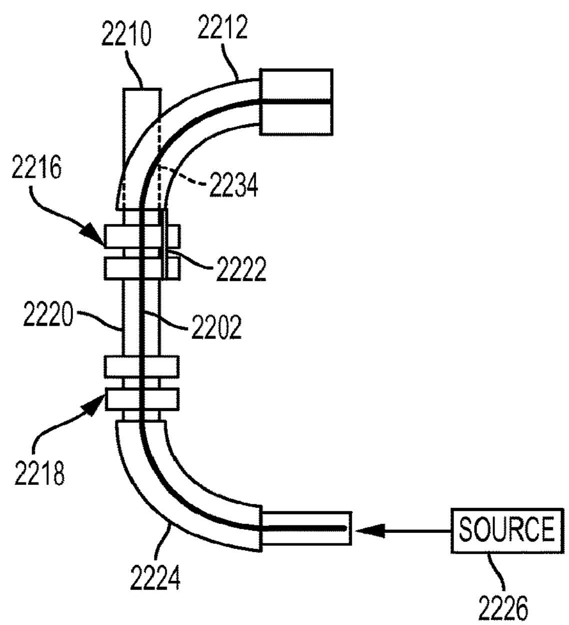

Although embodiments have been described above using a pair of beam tubes that move relative to each other in order to allow vertical displacement of the irradiation nozzle, other configurations using a single beam tube are also possible according to one or more contemplated embodiments. For example, FIGS. 22A-22B illustrate a beam transport assembly that includes a single beam tube 2220. In FIG. 22A, the beam transport assembly is shown in an expanded configuration with a first deflector 2224 (e.g., bending magnets) spaced at a first vertical distance from a second deflector 2212 (e.g., bending magnets). Thus, the particle beam from the source 2226 enters the beam transport assembly and is deflected by the first deflector 2224 to travel along the beam tube 2220 toward the second deflector 2212. The second deflector 2212 can further deflect the particle beam exiting the beam tube 2220 at a top end 2210 thereof to the irradiation nozzle (not shown).

As with previous embodiments, a first set of beam control optics 2216 (e.g., focusing magnets) and a second set of beam control optics 2218 (e.g., focusing magnets) can be disposed along a length of the beam tube 2220. The first set of beam control optics 2216 can be coupled to the second deflector 2212, for example, by a coupling 2222, that allows the first set of beam control optics 2216 to move with the second deflector 2212. Thus, the distance between the first set of beam control optics 2216 and the second set of beam control optics 2218 can vary as the position of the second deflector 2212 changes.

The beam tube 2220 can have a length sufficient to accommodate the displacement of the second deflector 2212 necessary to provide the desired irradiation coverage (e.g., a stroke length of at least 300 cm). For example, the particle beam 2202 may exit at an end 2210 of the beam tube 2220 when the beam transport assembly is in an expanded configuration, as shown in FIG. 22A. When the beam transport assembly transitions to the contracted configuration, the second deflector 2212 moves toward the first deflector 2224. Since the beam tube 2220 is of fixed length, the second deflector 2212 moves with respect to the beam tube 2220 along an axis thereof and causes the particle beam 2202 to exit the beam tube through a wall 2234 of the beam tube, as illustrated in FIB. 22B. The beam tube 2220 can be made of a material and/or have a sufficiently thin wall so as to allow the particle beam 2202 contained therein to penetrate the wall of the beam tube 2220 with minimal scattering effect.

Alternatively or additionally, the beam tube 2220 may be coupled to the second deflector 2212 so as to move together. In such a configuration, the particle beam 2202 from the source 2226 can be deflected by the first deflector 2224 to enter the beam tube 2220 through a wall thereof, similar to the manner in which the particle beam exits the beam tube in FIG. 22B. In yet another alternative, the position of the beam tube 2220 remains fixed and the first and second deflectors 2224, 2212 can move with respect to the beam tube 2220 along an axis thereof. The first and second deflectors 2224, 2212 may cause the particle beam 2202 to enter/exit the beam tube 2220 at respective ends of the beam tube or through a respective portion of the wall of the beam tube 2202, depending on the position of the deflectors with respect to the beam tube.

It is also possible according to one or more contemplated embodiments for the beam transport assembly to convey a particle beam through a non-vacuum environment (e.g., through air or a particular gas or gas mixture that minimizes scattering, such as but not limited to, helium) along at least a portion of the beam path between the particle beam source and the irradiation nozzle. For example, in any of the embodiments herein where components of the beam transport assembly (e.g., the beam tube(s)) are under vacuum, an air or gas environment can be provided instead of the vacuum, or the vacuum component or beam tube(s) may be omitted altogether. Any scattering that may result from travel through the non-vacuum environment may be compensated by appropriate control (e.g., magnetic field strength) and/or displacement (e.g., location along the beam path) of the focusing and/or deflecting magnets. Such scattering may be particularly low when the beam transport assembly is in a short or contracted state.

In some embodiments, a vacuum along the beam path can be maintained when the beam transport assembly is in a longer or expanded state and scattering may otherwise present an issue. When the beam transport assembly is in a shorter or contracted state, a non-vacuum environment can be allowed and any resulting scattering controlled by the focusing and/or deflecting magnets.

In one or more first embodiments, a beam transport assembly for conveying a particle beam comprises a first beam tube, a second beam tube, one or more first focusing magnets, one or more second focusing magnets, and an expandable portion. The first beam tube has a first interior volume maintained under vacuum. The second beam tube has a second interior volume maintained under vacuum. The second beam tube is axially spaced from the first beam tube. The one or more first focusing magnets are arranged along the first beam tube, and the one or more second focusing magnets are arranged along the second beam tube. The expandable portion couples the first beam tube to the second beam tube such that the particle beam can be conveyed therebetween. The expandable portion is configured to accommodate changed positions of the first and second beam tubes with respect to each other so as to alter a path length for the particle beam through the beam transport assembly.

In the first embodiments or any other embodiment, the expandable portion is configured to change length so as to alter the path length for the particle between the first and second focusing magnets.

In the first embodiments or any other embodiment, the one or more first focusing magnets and the one or more second focusing magnets comprise quadrupole magnets.

In the first embodiments or any other embodiment, the one or more first focusing magnets are coupled to and move with the first beam tube.

In the first embodiments or any other embodiment, the first beam tube has an outer diameter smaller than an inner diameter of the second beam tube, and the expandable portion comprises a first sliding seal between the first beam tube and the second beam tube. The first beam tube is configured to slide into the second interior volume to reduce the path length for the particle beam.

In the first embodiments or any other embodiment, the expandable portion comprises a second sliding seal between the first beam tube and the second beam tube. The second sliding seal is axially spaced from the first sliding seal. A differential pump is coupled to a volume between the first and second sliding seals.

In the first embodiments or any other embodiment, the expandable portion comprises a vacuum vessel disposed between the first and second beam tubes and constructed to rotate with respect to the first and second beam tubes.

In the first embodiments or any other embodiment, the vacuum vessel has a height that varies in a direction parallel to axes of the first and second beam tubes.

In the first embodiments or any other embodiment, the first beam tube is coupled to the vacuum vessel by a first rotating seal disposed at an axially first end of the vacuum vessel, and the second beam tube is coupled to the vacuum vessel by a second rotating seal disposed at an axially opposite second end of the vacuum vessel. The first and second rotating seals are constructed to rotate about a first rotation axis parallel to said axes of the first and second beam tubes. The first rotation axis is spaced from the axes of the first and second beam tubes in a direction perpendicular thereto.

In the first embodiments or any other embodiment, the vacuum vessel is constructed to rotate about a second rotation axis perpendicular to axes of the first and second beam tubes such that a path length through an interior volume of the vacuum vessel varies.

In the first embodiments or any other embodiment, respective ends of the first and second beam tubes proximal to the vacuum vessel include a vacuum window or foil, and a circumferential surface of the vacuum vessel facing said ends of the first and second beam tubes comprises a vacuum window or foil.

In the first embodiments or any other embodiment, the expandable portion comprises a gas-filled vessel disposed between the first and second beam tubes.

In the first embodiments or any other embodiment, the gas-filled vessel comprises a flexible structure such that a change in path length through the vessel is achieved by compressing or expanding the flexible structure.

In the first embodiments or any other embodiment, respective ends of the first and second beam tubes proximal to the gas-filled vessel include a vacuum window or foil, and a circumferential surface of the gas-filled vessel facing said ends of the first and second beam tubes comprise a window or foil.

In the first embodiments or any other embodiment, the vessel is filled with helium.

In one or more second embodiments, a system for irradiating an object with a particle beam comprises a beam transport assembly, an irradiation nozzle, a support, and a controller. The beam transport assembly conveys the particle beam from a particle source along a substantially vertical direction and redirects the particle beam to a horizontal input. The irradiation nozzle is coupled to the beam transport assembly to receive the particle beam at the horizontal input. The irradiation nozzle is configured to redirect the particle beam toward the object and to rotate about a swivel axis at the horizontal input. The support is constructed to support the object with respect to the irradiation nozzle and to move horizontally in a plane perpendicular to the swivel axis. The controller is configured to coordinate movements of the beam transport assembly, the irradiation nozzle, and the support. The beam transport assembly is constructed to change a path length of the particle beam so as to follow a vertical location of the swivel axis of the irradiation nozzle with respect to the support, and the controller is configured to coordinate the path length change of the particle beam, rotation of the irradiation nozzle about the swivel axis, and/or horizontal motion of the support to provide irradiation of the supported object from various angles in the plane perpendicular to the swivel axis while maintaining the irradiation nozzle at a constant distance from the supported object.

In the second embodiments or any other embodiment, the irradiation nozzle is configured to redirect the particle beam 90° from a direction of the particle beam at the horizontal input.

In the second embodiments or any other embodiment, the supported object is a patient, and the system is configured to deliver the particle beam as part of particle therapy for the patient.

In the second embodiments or any other embodiment, the swivel axis and a direction of propagation of the particle beam at the horizontal input are coincident.

In the second embodiments or any other embodiment, the controller is configured to coordinate the path length change of the particle beam, rotation of the irradiation nozzle about the swivel axis, and/or horizontal motion of the support to provide 360° of irradiation around the supported object.

In the second embodiments or any other embodiment, the beam transport assembly comprises one or more focusing magnets.

In the second embodiments or any other embodiment, the controller is configured to control a magnetic field of the one or more focusing magnets responsive to changes in path length of the particle beam.

In the second embodiments or any other embodiment, the controller comprises memory storing a lookup table that correlates changes in path length of the particle beam to control values for the magnetic field of the one or more focusing magnets.

In the second embodiments or any other embodiment, the system comprises a sensor that monitors the particle beam as the path length changes and provides a feedback signal to the controller. The controller is configured to control the magnetic field of the one or more focusing magnets responsive to the feedback signal.

In the second embodiments or any other embodiment, the support is further constructed to move horizontally and/or vertically in a plane parallel to the swivel axis.

In the second embodiments or any other embodiment, the beam transport assembly comprises a first dipole magnet that redirects the particle beam from the particle source along a vertically extending portion of the beam transport assembly and a second dipole magnet that redirects the particle beam to the horizontal input.

In the second embodiments or any other embodiment, the beam transport assembly comprises a first beam tube, a second beam tube, and an expandable portion. The first beam tube has a first interior volume maintained under vacuum. The second beam tube has a second interior volume maintained under vacuum. The second beam tube is axially spaced from the first beam tube. The expandable portion couples the first beam tube to the second beam tube such that the particle beam can be conveyed therebetween. The change in path length of the particle beam is accommodated by the expandable portion.

In the second embodiments or any other embodiment, the first beam tube has an outer diameter smaller than an inner diameter of the second beam tube, and the expandable portion comprises a first sliding seal between the first beam tube and the second beam tube. The first beam tube is configured to slide into the second interior volume to reduce the path length for the particle beam.

In the second embodiments or any other embodiment, the expandable portion comprises a vacuum vessel disposed between the first and second beam tubes and constructed to rotate with respect to the first and second beam tubes. The vacuum vessel has a height that varies in a direction parallel to axes of the first and second beam tubes. The first beam tube is coupled to the vacuum vessel by a first rotating seal disposed at an axially first end of the vacuum vessel, and the second beam tube is coupled to the vacuum vessel by a second rotating seal disposed at an axially opposite second end of the vacuum vessel. The first and second rotating seals are constructed to rotate about a first rotation axis parallel to said axes of the first and second beam tubes. The first rotation axis is spaced from the axes of the first and second beam tubes in a direction perpendicular thereto.

In the second embodiments or any other embodiment, the expandable portion comprises a vacuum vessel disposed between the first and second beam tubes and constructed to rotate with respect to the first and second beam tubes. The vacuum vessel is constructed to rotate about a second rotation axis perpendicular to axes of the first and second beam tubes such that the path length of the particle beam through an interior volume of the vacuum vessel varies.

In the second embodiments or any other embodiment, the expandable portion comprises a gas-filled vessel disposed between the first and second beam tubes. The gas-filled vessel is a flexible structure such that a change in path length through the vessel is achieved by compressing or expanding the flexible structure. The vessel is filled with helium.

In the second embodiments or any other embodiment, the beam assembly has a single beam tube formed of a material or having a thickness that allows the particle beam to pass through a wall of the single beam tube.

In one or more third embodiments, a method for irradiating an object comprises conveying a particle beam from a particle source along a beam transport assembly to a horizontal input of an irradiation nozzle, redirecting the particle beam from the horizontal input within the irradiation nozzle and directing the particle beam from the irradiation nozzle to irradiate the object arranged on a support from a first position, and changing a path length of the particle beam in the beam transport assembly so as to follow a vertical location of a swivel axis of the irradiation nozzle with respect to the support. The irradiation nozzle is configured to rotate about the swivel axis at the horizontal input.

In the third embodiments or any other embodiment, the method further comprises, responsively to the changing a length, altering a magnetic field strength of one or more focusing magnets of the beam transport assembly.

In the third embodiments or any other embodiment, the altering a magnetic field strength comprises selecting a control value for the magnetic field strength from a lookup table stored in memory based on a length of the beam transport assembly.

In the third embodiments or any other embodiment, the altering a magnetic field strength is responsive to a feedback signal from a sensor that monitors the particle beam.

In the third embodiments or any other embodiment, the supported object is a patient, and the irradiation is part of a particle therapy for the patient.

In the third embodiments or any other embodiment, the beam transport assembly comprises a first beam tube, a second beam tube, and an expandable portion. The first beam tube has a first interior volume maintained under vacuum. The second beam tube has a second interior volume maintained under vacuum. The second beam tube is axially spaced from the first beam tube. The expandable portion couples the first beam tube to the second beam tube such that the particle beam can be conveyed therebetween.

In the third embodiments or any other embodiment, the first beam tube has an outer diameter smaller than an inner diameter of the second beam tube. The expandable portion comprises a first sliding seal between the first beam tube and the second beam tube. The first beam tube is configured to slide into the second interior volume to reduce the path length for the particle beam. The changing a path length of the particle beam comprises axially sliding one of the first and second beam tubes with respect to the other of the first and second beam tubes.

In the third embodiments or any other embodiment, the expandable portion comprises a vacuum vessel disposed between the first and second beam tubes and constructed to rotate with respect to the first and second beam tubes. The vacuum vessel has a height that varies in a direction parallel to axes of the first and second beam tubes. The first beam tube is coupled to the vacuum vessel by a first rotating seal disposed at an axially first end of the vacuum vessel, and the second beam tube is coupled to the vacuum vessel by a second rotating seal disposed at an axially opposite second end of the vacuum vessel. The first and second rotating seals are constructed to rotate about a first rotation axis parallel to said axes of the first and second beam tubes. The first rotation axis is spaced from the axes of the first and second beam tubes in a direction perpendicular thereto. The changing a path length of the particle beam comprises rotating the vacuum vessel about the first rotation axis while axially displacing the first and second beam tubes with respect to each other.

In the third embodiments or any other embodiment, the expandable portion comprises a vacuum vessel disposed between the first and second beam tubes and constructed to rotate with respect to the first and second beam tubes. The vacuum vessel is constructed to rotate about a second rotation axis perpendicular to axes of the first and second beam tubes such that a path length through an interior volume of the vacuum vessel varies. The changing a path length of the particle beam comprises rotating the vacuum vessel about the second rotation axis while axially displacing the first and second beam tubes with respect to each other.

In the third embodiments or any other embodiment, the expandable portion comprises a gas-filled vessel disposed between the first and second beam tubes. The gas-filled vessel is a flexible structure such that a change in path length through the vessel is achieved by compressing or expanding the flexible structure. The vessel is filled with helium. The changing a path length of the particle beam comprises compressing or expanding the flexible structure while axially displacing the first and second beam tubes with respect to each other.

In the third embodiments or any other embodiment, the beam transport assembly comprises a beam tube and at least one first bending magnet. The beam tube has an interior volume maintained under vacuum. The beam tube is formed of a material and/or has a thickness that allows the particle beam to pass through a wall thereof. The at least one first bending magnet redirects the particle beam from a direction parallel to an axis of the beam tube to an input of an irradiation nozzle. The at least one first bending magnet is configured to move along the beam tube in the direction parallel to the axis of the beam tube. The changing a path length of the particle beam comprises moving the at least one first bending magnet along the beam tube.

In the third embodiments or any other embodiment, the method further comprises, at a same time as the changing a path length of the particle beam, rotating the irradiation nozzle about the swivel axis and/or moving the support in a plane perpendicular to the swivel axis so as to irradiate the object from a second position. The second position is at a same distance from the object as the first position but at a different angle in the plane perpendicular to the swivel axis.

In one or more fourth embodiments, a non-transitory computer-readable storage medium and a computer processing system are provided. The non-transitory computer-readable storage medium is embodied with a sequence of programmed instructions for controlling a system to irradiate an object with a particle beam. The computer processing system executes the sequence of programmed instructions embodied on the computer-readable storage medium to cause the computer processing system to control one or more focusing magnets of a beam transport assembly to convey a particle beam from a particle source along the beam transport assembly to a horizontal input of an irradiation nozzle, to control one or more deflecting magnets to redirect the particle beam from the horizontal input within the irradiation nozzle and to direct the particle beam from the irradiation nozzle to irradiate the object arranged on a support from a first position, and to control the beam transport assembly to change a path length of the particle beam so as to follow a vertical location of a swivel axis of the irradiation nozzle with respect to the support. The irradiation nozzle is configured to rotate about the swivel axis at the horizontal input.

In the fourth embodiments or any other embodiment, the computer-readable storage medium further causes the computer processing system to, responsively to the change in path length of the particle beam, alter a magnetic field strength of the one or more focusing magnets of the beam transport assembly.

In the fourth embodiments or any other embodiment, the computer-readable storage medium further causes the computer processing system to select a control value for the altered magnetic field strength from a lookup table stored in memory based on the changed length of the beam transport assembly.

In the fourth embodiments or any other embodiment, the computer-readable storage medium further causes the computer processing system to alter the magnetic field strength responsive to a feedback signal from a sensor that monitors the particle beam.

In the fourth embodiments or any other embodiment, the computer-readable storage medium further causes the computer processing system to, at a same time as the changing a path length of the particle beam, control the irradiation nozzle to rotate about the swivel axis and/or control the support to move in a plane perpendicular to the swivel axis so as to irradiate the object from a second position, which is at a same distance from the object as the first position but at a different angle in the plane perpendicular to the swivel axis.

In one or more fifth embodiments, a beam transport assembly for conveying a particle beam comprises a beam tube and at least one first bending magnet. The beam tube has an interior volume maintained under vacuum. The beam tube is formed of a material and/or has a thickness that allows the particle beam to pass through a wall thereof. The at least one first bending magnet redirects the particle beam from a direction parallel to an axis of the beam tube to an input of an irradiation nozzle. The at least one first bending magnet is configured to move along the beam tube in the direction parallel to the axis of the beam tube.

In the fifth embodiments or any other embodiment, the beam transport assembly further comprises at least two focusing magnets arranged along the beam tube and spaced apart from each other in the direction parallel to the axis of the beam tube.

In the fifth embodiments or any other embodiment, one of the at least two focusing magnets is configured to move along the direction parallel to the axis of the beam tube relative to another of the at least two focusing magnets.

In the fifth embodiments or any other embodiment, the at least two focusing magnets comprise quadrupole magnets.

In the fifth embodiments or any other embodiment, the at least one first bending magnet is a first dipole magnet. The beam transport assembly further comprises a second dipole magnet that redirects the particle beam from the particle source along said beam tube in the direction parallel to the axis of the beam tube.

In the fifth embodiments or any other embodiment, the beam transport assembly further comprises at least two focusing magnets arranged along the beam tube and spaced apart from each other in the direction parallel to the axis of the beam tube. One of the at least two focusing magnets is coupled to and moves with one of the first and second dipole magnets.

In one or more sixth embodiments, a system is provided for performing any of the methods disclosed herein.

Although embodiments herein have been described with respect to delivering a particle beam as treatment for a patient, embodiments of the disclosed subject matter are not limited thereto. Rather, embodiments can include delivering a particle beam (e.g., protons or any other high energy particle) for irradiating an object or animal.

Although the beam transport assembly has been described herein as conveying the particle beam from the source to the irradiation nozzle, it is contemplated that other beam transport components can be provided between the source and the nozzle. In other words, the variable length beam transport assembly need not be directly adjacent to the source at one end and the irradiation nozzle at the other. For example, other beam transport components (e.g., fixed length beam tubes, steering magnets, bending magnets, and/or focusing magnets) can be provided between the source and the irradiation nozzle, with the variable length beam transport assembly serving as, for example, a partial leg of the beam path between the source and the irradiation nozzle.

In addition, the terms "horizontal" and "vertical" have been used herein to describe the relative locations and motions of different components of the disclosed embodiments. However, the embodiments are not limited to strictly horizontal and vertical directions. Where such descriptive terms are used, they are to include deviations therefrom. For example, "horizontal" can include directions that have a minor vertical component (e.g., up to 10%) and "vertical" can include directions that have a minor horizontal component (e.g., up to 10%).

Moreover, the terms "horizontal" and "vertical" have been used herein for convenience to described relative orientations of components and motions thereof and are not intended to limit an arrangement of the irradiation system with respect to gravity. Indeed, it is contemplated that in some embodiments of the disclosed subject matter, the vertical direction may extend perpendicular to the direction of gravity and the horizontal direction may extend parallel to the direction of gravity.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

In one or more embodiments of the disclosed subject matter, non-transitory computer-readable storage media and a computer processing systems can be provided. In one or more embodiments of the disclosed subject matter, non-transitory computer-readable storage media can be embodied with a sequence of programmed instructions for controlling an irradiation device to perform a particle therapy, the sequence of programmed instructions embodied on the computer-readable storage medium causing the computer processing systems to perform one or more of the disclosed methods.

It will be appreciated that the modules, processes, systems, and devices described above can be implemented in hardware, hardware programmed by software, software instruction stored on a non-transitory computer readable medium or a combination of the above. For example, a method for controlling an irradiation system to perform particle irradiation can be implemented, for example, using a processor configured to execute a sequence of programmed instructions stored on a non-transitory computer readable medium. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and devices can be implemented as a single processor or as a distributed processor. Further, it should be appreciated that the steps mentioned herein may be performed on a single or distributed processor (single and/or multi-core). Also, the processes, modules, and sub-modules described in the various figures of and for embodiments herein may be distributed across multiple computers or systems or may be co-located in a single processor or system. Exemplary structural embodiment alternatives suitable for implementing the modules, sections, systems, means, or processes described herein are provided below.

The modules, processes, systems, and devices described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the methods, processes, modules, devices, and systems (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or computer program products (software program stored on a non-transitory computer readable medium).

Furthermore, embodiments of the disclosed methods, processes, modules, devices, systems, and computer program product may be readily implemented, fully or partially, in software using, for example, object or object-oriented software development environments that provide portable source code that can be used on a variety of computer platforms. Alternatively, embodiments of the disclosed methods, processes, modules, devices, systems, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the methods, processes, modules, devices, systems, and computer program product can be implemented in hardware and/or software using any known or later developed systems or structures, devices and/or software by those of ordinary skill in the applicable art from the function description provided herein and with a general basic knowledge of particle beam irradiation systems, control systems, and/or computer programming arts.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, systems, devices, and methods for particle beam transport for subsequent irradiation. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A beam transport assembly for conveying a particle beam, the beam transport assembly comprising:

a first beam tube with a first interior volume maintained under vacuum;

a second beam tube with a second interior volume maintained under vacuum, the second beam tube being axially spaced from the first beam tube;

one or more first focusing magnets arranged along the first beam tube;

one or more second focusing magnets arranged along the second beam tube; and an expandable portion coupling the first beam tube to the second beam tube such that the particle beam can be conveyed therebetween, wherein the expandable portion is configured to accommodate changed positions of the first and second beam tubes with respect to each other so as to alter a path length for the particle beam through the beam transport assembly, and wherein the first beam tube has an outer diameter smaller than an inner diameter of the second beam tube, and the expandable portion comprises a first sliding seal between the first beam tube and the second beam tube, the first beam tube being configured to slide into the second interior volume to reduce the path length for the particle beam.

2. The beam transport assembly of claim 1, wherein the one or more first focusing magnets and the one or more second focusing magnets comprise quadrupole magnets.

3. The beam transport assembly of claim 1, wherein the one or more first focusing magnets are coupled to and move with the first beam tube.

4. The beam transport assembly of claim 1, wherein the expandable portion comprises a second sliding seal between the first beam tube and the second beam tube, the second sliding seal being axially spaced from the first sliding seal, and further comprising a differential pump coupled to a volume between the first and second sliding seals.

5. A beam transport assembly for conveying a particle beam, the beam transport assembly comprising:

a first beam tube with a first interior volume maintained under vacuum;

a second beam tube with a second interior volume maintained under vacuum, the second beam tube being axially spaced from the first beam tube;

one or more first focusing magnets arranged along the first beam tube;

one or more second focusing magnets arranged along the second beam tube; and an expandable portion coupling the first beam tube to the second beam tube such that the particle beam can be conveyed therebetween, wherein the expandable portion is configured to accommodate changed positions of the first and second beam tubes with respect to each other so as to alter a path length for the particle beam through the beam transport assembly, and wherein the expandable portion comprises a vacuum vessel disposed between the first and second beam tubes and constructed to rotate with respect to the first and second beam tubes.

6. The beam transport assembly of claim 5, wherein the vacuum vessel has a height that varies in a direction parallel to axes of the first and second beam tubes.

7. The beam transport assembly of claim 6, wherein the first beam tube is coupled to the vacuum vessel by a first rotating seal disposed at an axially first end of the vacuum vessel, and the second beam tube is coupled to the vacuum vessel by a second rotating seal disposed at an axially opposite second end of the vacuum vessel, the first and second rotating seals being constructed to rotate about a first rotation axis parallel to said axes of the first and second beam tubes, the first rotation axis being spaced from the axes of the first and second beam tubes in a direction perpendicular thereto.

8. The beam transport assembly of claim 5, wherein the vacuum vessel is constructed to rotate about a second rotation axis perpendicular to axes of the first and second beam tubes such that a path length through an interior volume of the vacuum vessel varies.

9. The beam transport assembly of claim 8, wherein respective ends of the first and second beam tubes proximate to the vacuum vessel include a vacuum window or foil, and a circumferential surface of the vacuum vessel facing said ends of the first and second beam tubes comprises a vacuum window or foil.

10. A beam transport assembly for conveying a particle beam, the beam transport assembly comprising:

a first beam tube with a first interior volume maintained under vacuum;

a second beam tube with a second interior volume maintained under vacuum, the second beam tube being axially spaced from the first beam tube;

one or more first focusing magnets arranged along the first beam tube;

one or more second focusing magnets arranged along the second beam tube; and an expandable portion coupling the first beam tube to the second beam tube such that the particle beam can be conveyed therebetween, wherein the expandable portion is configured to accommodate changed positions of the first and second beam tubes with respect to each other so as to alter a path length for the particle beam through the beam transport assembly, and wherein the expandable portion comprises a gas-filled vessel disposed between the first and second beam tubes, wherein the gas-filled vessel comprises a flexible structure such that a change in path length through the vessel is achieved by compressing or expanding the flexible structure.

11. The beam transport assembly of claim 10, wherein respective ends of the first and second beam tubes proximate to the gas-filled vessel include a vacuum window or foil, and a circumferential surface of the gas-filled vessel facing said ends of the first and second beam tubes comprise a window or foil.

12. The beam transport assembly of claim 10, wherein the vessel is filled with helium.

* * * * *